United States Patent
Andle et al.

(10) Patent No.: US 8,073,640 B2
(45) Date of Patent: Dec. 6, 2011

(54) CONTROLLED COMPRESSIONAL WAVE COMPONENTS OF THICKNESS SHEAR MODE MULTI-MEASURAND SENSORS

(75) Inventors: Jeffrey C. Andle, Falmouth, ME (US); Daniel S. Stevens, Stratham, NH (US); Reichl B. Haskell, Nashua, NH (US); Dana Y. G. Tucker, Acton, MA (US)

(73) Assignee: Delaware Capital Formation Inc., Wilmington, DE (US)

( * ) Notice: Subject to any disclaimer, the term of this patent is extended or adjusted under 35 U.S.C. 154(b) by 0 days.

(21) Appl. No.: 12/884,931

(22) Filed: Sep. 17, 2010

(65) Prior Publication Data

US 2011/0071776 A1 Mar. 24, 2011

Related U.S. Application Data

(60) Provisional application No. 61/243,685, filed on Sep. 18, 2009.

(51) Int. Cl.
*G06F 19/00* (2011.01)
*G01N 29/02* (2006.01)

(52) U.S. Cl. .......................................... 702/54; 73/24.06

(58) Field of Classification Search .................... 702/54, 702/50; 73/54.14, 579, 24.06
See application file for complete search history.

(56) References Cited

U.S. PATENT DOCUMENTS

| | | | |
|---|---|---|---|
| 4,175,243 A | 11/1979 | Corbett | |
| 4,312,228 A | 1/1982 | Wohltjen | |
| 4,535,631 A | 8/1985 | Sinha | |
| 4,769,882 A | 9/1988 | Rosen et al. | |
| 4,800,316 A | 1/1989 | Ju-Zhen | |
| 4,870,312 A | 9/1989 | La Rosa et al. | |
| 4,916,416 A | 4/1990 | Desbois | |
| 5,416,448 A | 5/1995 | Wessendorf | |
| 5,532,538 A | 7/1996 | Jin et al. | |
| 5,565,724 A | 10/1996 | Hachigo et al. | |
| 5,633,616 A | 5/1997 | Goto | |
| 5,708,191 A | 1/1998 | Greenwood et al. | |
| 5,741,961 A | 4/1998 | Martin et al. | |
| 5,793,146 A | 8/1998 | Wright | |
| 5,798,452 A | 8/1998 | Martin et al. | |

(Continued)

FOREIGN PATENT DOCUMENTS

DE 102006003649 A1 8/2007

(Continued)

OTHER PUBLICATIONS

EP Search Report dated Sep. 13, 2010 of Patent Application No. EP 09152744.0 filed Feb. 13, 2009.

(Continued)

*Primary Examiner* — Bryan Bui
(74) *Attorney, Agent, or Firm* — Vern Maine & Associates

(57) ABSTRACT

The current invention relates to a conductivity-dielectric (CD) electrode design with apertures that allow compressional waves to propagate away from the surface of the acoustic wave device unimpeded. This prevents reflection of compressional waves that would interact with the viscosity sensor surface, thus altering the device response. It allows compressional waves to pass through, and allows the dual mode viscosity sensor responses to be utilized for density/viscosity/elasticity measurement and correlation. The invention further offers methods of instrumentation to detect unwanted reflections, to compensate, and to correct for the distortions caused by reflections. Finally, the invention provides a system and method for utilizing deliberately introduced reflections to obtain additional information, including fluid density.

29 Claims, 20 Drawing Sheets

U.S. PATENT DOCUMENTS

| | | |
|---|---|---|
| 5,877,581 A | 3/1999 | Inoi et al. |
| 5,880,552 A | 3/1999 | McGill et al. |
| 5,886,250 A | 3/1999 | Greenwood |
| 6,006,589 A | 12/1999 | Rodahl |
| 6,033,852 A | 3/2000 | Andle et al. |
| 6,082,180 A | 7/2000 | Greenwood |
| 6,082,181 A | 7/2000 | Greenwood |
| 6,378,370 B1 | 4/2002 | Haskell et al. |
| 6,401,519 B1 | 6/2002 | McFarland et al. |
| 6,543,274 B1 | 4/2003 | Herrmann et al. |
| 6,567,753 B2 | 5/2003 | Potyrailo |
| 6,745,626 B2 | 6/2004 | Usui et al. |
| 6,788,620 B2 | 9/2004 | Shiraishi et al. |
| 6,969,943 B2 | 11/2005 | Hashimoto et al. |
| 6,989,625 B2 | 1/2006 | Suzuki et al. |
| 7,002,281 B2 | 2/2006 | Andle |
| 7,007,546 B2 | 3/2006 | Andle |
| 7,061,163 B2 | 6/2006 | Nagahara et al. |
| 7,075,216 B1 | 7/2006 | Vetelino |
| 7,181,957 B2 | 2/2007 | Andle |
| 7,219,537 B2 | 5/2007 | Andle |
| 7,267,009 B2 | 9/2007 | Liu et al. |
| 7,287,431 B2 | 10/2007 | Liu et al. |
| 7,383,731 B2 | 6/2008 | Liu et al. |
| 7,434,989 B2 | 10/2008 | Solie |
| 7,514,844 B2 | 4/2009 | Unkrich |
| 7,552,619 B2 | 6/2009 | Andle |
| 7,666,152 B2 | 2/2010 | Ein-Gal |
| 7,696,672 B2 | 4/2010 | Sugiura et al. |
| 7,936,110 B2 * | 5/2011 | Andle et al. .................. 310/333 |
| 2004/0135653 A1 | 7/2004 | Kidoh |
| 2005/0132784 A1* | 6/2005 | Andle .......................... 73/54.41 |
| 2006/0244346 A1 | 11/2006 | Iwata |
| 2007/0144240 A1 | 6/2007 | Andle |
| 2008/0100176 A1 | 5/2008 | Haskell et al. |
| 2008/0163694 A1 | 7/2008 | Haskell et al. |
| 2009/0216467 A1 | 8/2009 | Andle |
| 2009/0309453 A1 | 12/2009 | Andle |
| 2010/0052470 A1 | 3/2010 | Andle et al. |
| 2010/0231092 A1 | 9/2010 | Andle et al. |
| 2011/0036151 A1 | 2/2011 | Andle |

FOREIGN PATENT DOCUMENTS

| | | |
|---|---|---|
| EP | 0542469 A1 | 5/1993 |
| WO | 2005114138 A2 | 12/2005 |
| WO | 2007123537 | 11/2007 |
| WO | 2007123539 | 11/2007 |
| WO | 2009105354 A2 | 8/2009 |

OTHER PUBLICATIONS

Office Action dated Mar. 5, 2010 for U.S. Appl. No. 11/814,074, 16 pages.

Office Action dated Aug. 4, 2010 for U.S. Appl. No. 12/036,125, 12 pages.

Office Action dated Mar. 25, 2010 for U.S. Appl. No. 12/036,125, 19 pages.

Andle, et al., "Instrumentation of Acoustic Wave Devices", U.S. Appl. No. 12/540,339, filed Aug. 12, 2009, 52 pages.

Andle, et al. "Improved Measurement of Fluid Parameters", U.S. Appl. No. 12/780,869, filed May 15, 2010, 50 pages.

Schweyer, M. et al., "A Novel Monolithic Piezoelectric Sensor", IEEE International Ultrasonics Symposium, 1997, pp. 371-374.

Schweyer, M. et al. "A Novel Monolithic Piezoelectric Sensor", IEEE International Frequency Control Symposium, 1997, pp. 32-40.

Andle, J. et al., "Design, Packaging and Characterization of a Two-Port Bulk Wave Langasite Viscometer", IEEE Sensors 2007, pp. 868-871.

Durdag, K. et al., "Portable/Handheld Oil Assessment Device Project: NCMS Collaborative Agreement No. 200640-140414", Final Report, Nov. 12, 2007. (Unpublished).

Durdag, K. et al., "Real-Time Viscosity Measurement for Condition-Based Monitoring Using Solid-State Viscosity Sensor", Tribology Transactions, 51:296-302, 2008.

Andle, J. et al., "Threaded Fluid Condition Sensor for Real-Time, On-Line and In-Line Oil Conditioning Monitoring", SENSOR+TEST 2009 Conference, Nuremberg, Germany, May 26-28, 2009, vol. II; pp. 229-234.

Office Action dated Nov. 16, 2010 for U.S. Appl. No. 12/404,288, 10 pages.

Andle, J. et al., "Electrically Isolated Thickness Shear Mode Liquid Phase Sensor for High Pressure Environments", IEEE Ultrasonics Symposium, 2008, pp. 1128-1133.

Barlow et al., "The Visco-Elastic Behaviour of Lubricating Oils Under Cyclic Shearing Stress", Proc. R. Soc. Lond. A., 1959, pp. 52-69, vol. 253.

Baer, R.L., "STW Chemical Sensors", Proc. 1992 Ultrasonics Symp., pp. 293-298 (1991).

Inoue, T. et al., "Miniaturization of Angular Rate Sensor Element Using Bonded Quartz Tuning Fork", Proceedings of the 2003 IEEE International Frequency Control Symposium and PDA Exhibition Jointly with the 17th European Frequency and Time Forum.

Ballato, Arthur, "The Stacked-Crystal Filter", Proceedings, 1975 IEEE International Symposium on Circuits and Systems, Apr. 1975, IEEE.

Gandsas et al., "Advanced Therapy in Minimally Invasive Surgery", (Talmini, 2006 BC Decker, of Hamilton, ON Canada, ISBN 1-55009-238-3).

Hata et al., "Unidirectional Surface-Acoustic-Wave Transducer with Meander and Interdigital Electrodes", Electronics and Communications in Japan, vol. 61, Jul. 1978, pp. 52-60.

Lindenbauer, T. et al., "Two-Dimensional Closed Form Analysis of TSM Quartz Resonators", Vienna University of Technology, Institute of Sensor and Actuator Systems. Presented Eurosensor XIX Barcelona Spain, Sep. 2005. Downloaded from http://www-samlab.unine.ch/ConferenceCD/EuroSensorsXIX/pdfs/TB14.pdf.

Hickernell, Fred, "The Characterization of Permanent Acoustic Bonding Agents", IEEE Frequency Control Symposium Proceedings, 2008, 4 pgs.

Lucklum, Ralph et al., "Thin Film Shear Modulus Determination With Quartz Crystal Resonators: A Review", IEEE International Frequency Control Symposium and PDA Exhibition, 2001, pp. 408-418.

Morray, Boima et al., "PMMA Polymer Film Characterization Using Thickness-Shear Mode (TSM) Quartz Resonator", IEEE International Frequency Control Symposium and PDA Exhibition, 2002, pp. 294-300.

Gouws, G.J. et al., "Measurement of the Equivalent Circuit Parameters of Chemical Interface Layers on Bulk Acoustic Wave Resonators", IEEE International Frequency Control Symposium and Exposition, 2004, pgs. 311-316.

Cernosekt, R.W. et al., "Comparison of Lumped-Element and Transmission-Line Models for Thickness-Shear-Mode Quartz Resonator Sensors", IEEE International Frequency Control Symposium, 1997, pp. 96-104.

Stevens, D. et al., "An Analysis of SC-Cut Quartz Trapped Energy Resonators with Rectangular Electrodes", 35th Annual IEEE Frequency Control Symp., 1981, pp. 205-212

Paul, H.S. et al., "Forced Torsional Vibrations of a Semi-Infinite Piezoelectric Medium of (622) Class", Department of Mathematics, Indian Institute of Technology, Downloaded from www.new.dli.ernet.in/rawdataupload/insa/INSA_2/20005ad4_362.pdf.; Jun. 1978; pp. 362-368.

Hongyu, Wei Pang et al., "Self-Aligned Lateral Field Excitation Film Acoustic Resonator With Very Large Electromechanical Coupling", IEEE International Ultrasonics, Feroelectronics, and Frequency Control Joint 50th Anniversary Conference, 2004, pp. 558-561.

Abe, Hiroshi et al., "Energy Trapping of Thickness Shear Vibrations Excited by Parallel Electric Field and its Application to Piezoelectric Vibratory Gyroscopes", IEEE Ultrasonic Symposium, 1998, pp. 467-471.

Zhang, C. et al, "Three Modes of Operation of an Acoustic Wave Device with Lateral Field Excitation Structure", IEEE Ultrasonics Symposium, 2008, pp. 443-446.

McCann, D. et al., "The Detection of Chemical and Biological Analytes Using a Monolithic Spiral Coil Acoustic Transduction Sensor", IEEE Ultrasonics Symposium, 2008, pp. 1187-1190.

Zhang, C. et al, "Novel Electrode Configurations of Lateral Field Excited Acoustic Wave Devices on (yxl)-58° LINbO3", IEEE Ultrasonics Symposium, 2008, pp. 276-279.

Andle, J. et al., "Mitigating Spurious Compressional Waves in Multi-Measurand Thickness Shear Mode Sensors", IEEE UFFC, 2009, pp. 2519-2524.

Andle, J. et al., "Improved Substrate Selection for Lateral Field TSM Sensors", IEEE UFFC, 2009, pp. 649-654.

Tessier et al., "Effects of the Generation of Compressional Waves on the Response of the Thickness-Shear Mode Acoustic Wave Sensor in Liquids", Anal. Chem., 1994, pp. 3569-3574, vol. 66.

Cernosek et al., "Comparison of Lumped-Element and Transmission-Line Models for Thickness-Shear-Mode Quartz Resonator Sensors", IEEE Trans. UFFC, 1998, pp. 1399-1407.

Kim, Yonkee et al., "Doubly Rotated Resonators for Sensing the Properties of Liquids", IEEE Ultrasonic Symposium, 2003, pp. 53-55.

PCT Search Report dated Mar. 30, 2011 of Patent Application No. PCT/US2010/049317 filed Sep. 17, 2010.

Office Action dated Mar. 9, 2011 for U.S. Appl. No. 12/202,431, 7 pages.

Martin, S.J. et al., "Characterization of a Quartz Crystal Microbalance with Simultaneous Mass and Liquid Loading", Anal. Chem., vol. 63, No. 20, Oct. 15, 1991, pp. 2272-2281.

Arnau, A., Jiminez, Y, Sogorb, T.; "Thickness Shear Mode Quartz Crystals in Viscoelastic Fluid Media", Journal of Applied Physics, vol. 88, No. 8, Oct. 15, 2000, pp. 4498-4506, 2000.

Martin S. J., Frye, G. C., Cemosek, R. W. and Senturia, S. D., "Microtextured Resonators for Measuring Liquid Properties", Proc. 1994 Solid-State Sensor and Actuator Workshop, 6 pgs., Hilton Head, SC.

Ballatro, Arthur, "Stacked Crystal Filters", Proceedings 1975 IEEE International Symposium on Circuits and Systems, Apr. 21-23, 1975, pp. 301-304.

Shankar, Shri S., "Well Logging Techniques and Formation Evaluation—an Over View"—30 pages, Petroleum Federation of India, Petrofed, Industry-Academia Workshop on "Technology Imperatives for Exploration and Production of Oil & Gas" Mar. 17-20, 2010.

* cited by examiner

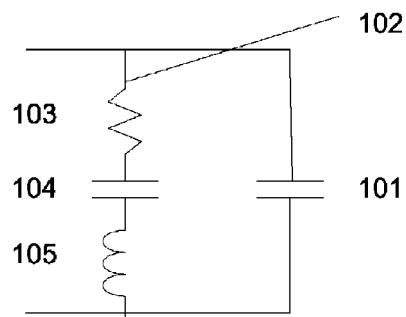
(a)
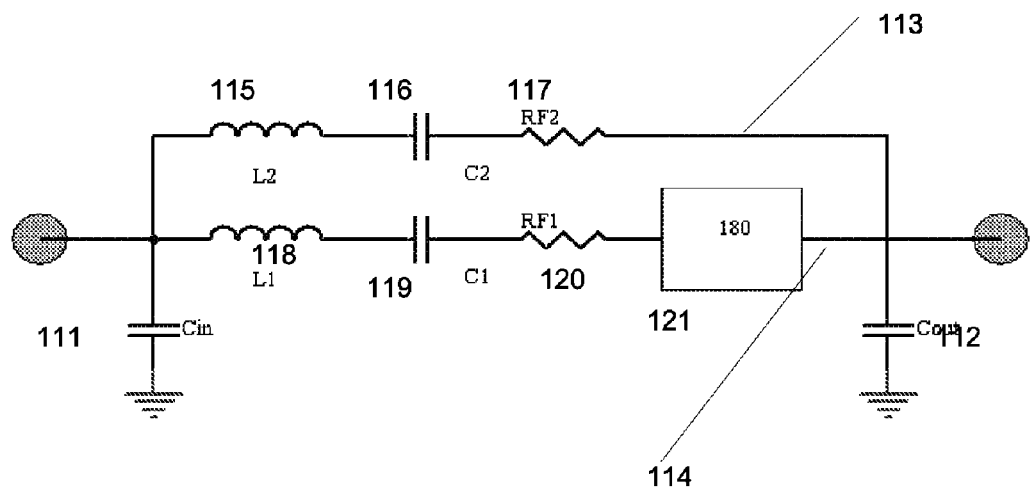
(b)
Fig. 1 Prior Art

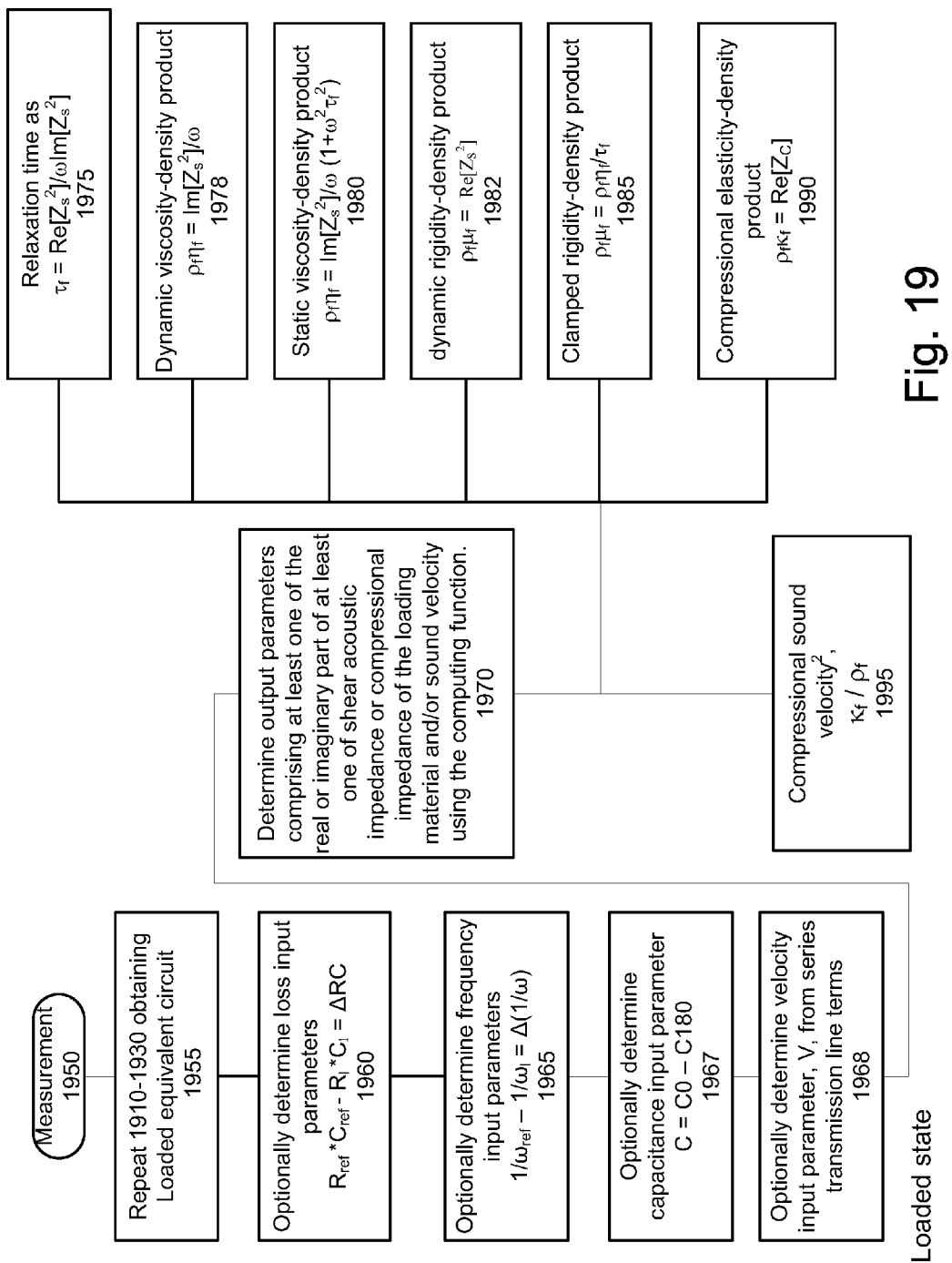

CONTROLLED COMPRESSIONAL WAVE COMPONENTS OF THICKNESS SHEAR MODE MULTI-MEASURAND SENSORS

This application claims the benefit of U.S. Provisional Application No. 61/243,685 filed Sep. 18, 2009, this application is herein incorporated by reference in its entirety for all purposes; U.S. application Ser. No. 12/036,125 filed Feb. 22, 2008 entitled "Sensor, System, and Method for Measuring Fluid Properties Using Multi-Mode Quasi-Shear-Horizontal Resonator"; U.S. application Ser. No. 12/540,339 filed Aug. 12, 2009 entitled "Instrumentation of Acoustic Wave Devices"; U.S. application Ser. No. 12/780,869 filed May 15, 2010 entitled "Improved Measurement of Fluid Parameters"; U.S. application Ser. No. 12/780,868 filed May 15, 2010 entitled "Improved Calibration of High Frequency Fluid Phase Acoustic Sensors"; U.S. application Ser. No. 11/814,074 entitled "Electro Acoustic Sensor for High Pressure Environments" to Andle filed Apr. 20, 2006; U.S. application Ser. No. 12/202,431 entitled "Asymmetric Composite Acoustic Wave Sensor" to Andle and Haskell filed Sep. 2, 2008; and U.S. application Ser. No. 12/404,288, entitled 'Improved Lateral Excitation of Pure Shear Modes', to Andle, Haskell, and Stevens filed Mar. 14, 2009 are herein incorporated in their entireties by reference.

FIELD OF THE INVENTION

The invention relates to measuring physical properties of fluid samples. More specifically, the invention relates to devices, systems, and methods for simultaneously determining density, shear viscoelasticity, and compressional elasticity measurement & correlation properties of a material such as lubricating oil or fuels.

BACKGROUND OF THE INVENTION

There is a growing demand for multi-measurand measurement of fluid properties in industrial settings. A notable example is in the monitoring of fuels, lubricants, hydraulic fluids, and coolants in which fluid aging and fluid contamination must be monitored and subjected to trend analysis to optimize preventive maintenance schedules. Typically these applications require viscosity measurement for immediate detection of catastrophic failure and employ conductivity and/or dielectric measurements for predictive measurements. Often, the measurement principles most amenable to in situ measurement have several secondary effects that distort the measurements from those obtained using lab equipment. Furthermore, other fluid physical properties are often desired in order to qualify the cause of a viscosity change.

Despite over 20 years of effort to develop a low-cost, high performance, multi-measurand fluid condition sensor, there is no single measurement approach that is suited to simultaneously detecting all of the fluid properties of interest for lubricants, fuels, hydraulic fluids, and coolants, such as fuel dilution, soot loading, water and glycol contamination, additives depletion, and wear particle detection.

While many approaches have been proposed to monitor these properties, vibrating sensors—especially the solid state implementations based on piezoelectric devices that impart acoustic energy onto the fluid—have shown the most promise. Generally, the measurable parameters are non-linear functions of a harmonic frequency, $\omega$, and the driving signal amplitude of the sensor. Since the functional forms are known, and since the prior art provides methods of instrumentation of the frequency dependence and amplitude dependence, it is possible to address these effects. Using the prior art in conjunction with the present invention, it is possible to characterize the dependence in some applications and possible to correct the values back to laboratory conditions in other applications. Of particular interest is the rheology of a fluid, specifically the relationship between shear stress and the rate of shear strain as a function of the rate of shear strain and the harmonic frequency of shear strain. Many pseudoplastic models are well known in the literature.

For clarity, this application will refer to such vibrating piezoelectric device based sensors as Acoustic Wave Device or AWD. A resonant AWD is considered herein a device comprising a crystalline material having a plurality of electrodes that provides movement of the crystal face in response to electrical power presented between at least an input pair of these electrodes, and conversely generates an electrical signal at an output pair of electrodes in response to power applied to the crystal face. One or more electrodes may be common to both input and output pairs, and the input pair may also serve as the output pair. The term extends to Thickness Shear Mode (TSM), Surface Acoustic Wave (SAW), Surface Transverse Wave (STW), Bulk Acoustic Wave (BAW), Quartz Crystal Microbalance (QCM) and the like. An AWD may operate using plate mode, thickness mode, shear mode and shear thickness mode, bulk wave, love wave, and the like, and may utilize any convenient cut or material. Quartz, langasite, langatate, gallium phosphate, lithium niobate, and lithium tantalate are widely reported for sensor applications using AWD, and many newer materials are expected to have promise in this emerging field that expressly fall within the AWD definition. It is noted that a single AWD commonly has more than one resonant frequency, each equivalently related to as a 'mode' or a 'resonant mode'. Furthermore, even devices designed to be 'single mode' devices have unwanted, spurious modes.

Obtaining information about the environment in which the AWD operates makes the AWD into a sensor. However, the sensor needs to be coupled to equipment—circuitry, computing device, and the like so as to provide useful information. The connection method, support circuitry, and manners of decoding the information are colloquially known as the 'instrumentation' of a device, and providing said instrumentation is known as 'instrumenting' the device.

Numerous piezoelectric acoustic wave device (AWD) technology based sensors are known that potentially satisfy at least subsets of the need. By way of example, quartz tuning forks were disclosed in U.S. Pat. No. 6,401,519 to McFarland et al., corrugated thickness shear mode (TSM) sensors were disclosed in U.S. Pat. No. 5,741,961 by Martin et al., and corrugated surface transverse wave (STW, Love mode) were disclosed by Hermann et al. in U.S. Pat. No. 6,543,274. The monolithic piezoelectric sensor (MPS) of Andle as taught in U.S. Pat. No. 6,033,852, the corrugated MPS of Andle as described in U.S. Pat. No. 7,552,619, the high pressure composite resonators of Andle as described in US Patent publication 2009-0309453 and US patent publication 2010-0052470-A1, the multi-mode, quasi-shear horizontal resonator (MMQSHR) of Andle, as disclosed in US Patent publication 2009/0216467 and WO2009/105354, the lateral field excited TSM of Vetelino as disclosed in U.S. Pat. No. 7,075,216, and the coplanar circularly polarized transducer (CCPT) of Andle, as disclosed in U.S. patent application Ser. No. 12/404,288 constitute newer examples. The CCPT comprises a plurality of electrodes formed on a common surface (planar or curvilinear) such that one or more electrodes form a functionally closed shape, the plurality of electrodes forming a plurality of shapes, each of those shapes being functionally fully enclosed by, or fully enclosing, another shape and defining a gap therebetween. The electrodes therein are defined as coplanar circularly polarized electrodes (CCPE) and a CCPT comprises a plurality of coplanar circularly polarized electrodes separated by at least one gap therebetween. 'Functionally closed shape' implies that a small gap or gaps in the shape may be introduced that, while geometrically breaking the closed shape, will have minimal effect on the circular polarization induced by the CCPT. This transducer may be applied to a variety of AWD's but is most effective while used to create lateral field excitation in a thickness shear mode (TSM) device.

All the above identified patents, patent publications, and patent applications are incorporated herein by reference in their entirety.

Early work by Sandia National Laboratories and others, S. J. Martin, V. E. Granstaff and G. C. Frye, "Characterization of a Quartz Crystal Microbalance with Simultaneous Mass and Liquid Loading", Anal Chem 1991, 63, 2272-2281, demonstrated both the applicability and limitations of quartz thickness shear mode (TSM) sensors. Five significant limitations of the early TSM sensors are (a) the time constant of the static capacitance in parallel with the motional resistance limits measurement range and resolution, (b) the low piezoelectric coupling ($k^2$) of quartz limits measurement range of the motional resistance for a given instrumentation system, (c) Maxwellian properties of real fluids deviate substantially from the Newtonian model above ~1 MHz for typical hydrocarbons and (d) incidental compressional wave components that are inherent to TSM energy trapping are known to cause an erroneous reading of the viscous losses, and (e) reflections of these compressional waves from an opposing surface establish resonances within the fluid between the crystal face and an adjacent reflective surface.

A quartz-based monolithic crystal filter (MCF) was introduced by Schweyer et al. in 1997, M. Schweyer, J. Hilton, J. Munson, J. Andle, J. Hammond, R. Lec & Q. Lin, "A Novel Monolithic Piezoelectric Sensor", 1997 IEEE International Ultrasonics Symposium, pp. 371-374 and M. Schweyer, J. Hilton, J. Munson, J. Andle, J. Hammond and R. Lec, "A novel monolithic piezoelectric sensor", 1997 IEEE International Frequency Control Symposium, pp. 32-40, as a solution to the parallel loading of the static capacitance of single port TSM devices. The topology of the MCF places the static capacitance as two shunt elements in parallel with the source and load resistances and not in parallel with transmission through the motional circuit, extending the constraints of (a), above.

In order to ease measurements of fluid parameters utilizing a resonant AWD, it is well known to model the device after an equivalent electrical circuit or transmission lines which approximately relate one or more simplified measurable electrical parameters to one or more physical properties of the fluid. It is common to model the behavior of the AWD in a single resonant frequency by a simple equivalent electrical series resonance circuit comprising a resistance $R_m$, inductance $L_m$, and capacitance $C_m$, connected in series. The subscript, m, denotes a motional property seen through the acoustic to electrical "transformer ratio" of the piezoelectric effect. Such reduced equivalent circuit models are employed for computational simplicity and conceptual clarity.

FIG. 1.a shows the equivalent circuit of the prior art single-port TSM and FIG. 1.b shows the equivalent circuit of the prior art Monolithic Piezoelectric Sensor, more recently embodied as a Multi-Mode Quasi-Shear-Horizontal Resonator (MMQSHR). In the original TSM, the physical static capacitance 101 of the electrodes is in parallel with the resonant transmission path 102, represented by series motional resistance 103, motional capacitance 104, and motional inductance 105. In the MMQSHR the static capacitance is split into an input 111 and output 112 capacitance, neither of which is in shunt with the transmission paths 113 and 114. Transmission path 113 has 0° of phase shift at its series resonance and is modeled by a motional inductance 115, capacitance 116, and resistance 117. Transmission path 114 has 180° of phase shift at its series resonance and is modeled by a motional inductance 118, capacitance 119, and resistance 121 with a 180° phase shifter 121.

This relocation of the physical capacitance precludes the need for complex compensation schemes and also allows operation of a TSM sensor with isolated electrical connections impervious to electrical perturbations by the fluid. Furthermore, the use of a low source impedance excitation circuit and a low load impedance current measurement detector allows the measurement of the transfer admittance, $Y_{21}$, of the element, eliminating the residual effects of these physical transducer static capacitance elements.

A swept frequency transmission circuit may be employed to extract the motional resistance from the sampled transfer function data and track the resonant frequency over perturbations due to pressure, temperature, and viscosity. A number of methods allow the measurement of the real part of the transfer function. The transfer function might be $S_{21}$ as measured by a vector network analyzer, H(F) as measured by the detected RMS voltages, or $Y_{21}$ as the ratio of the short output circuit current to the input voltage. For a 50Ω load, a sufficiently small static capacitance and a sufficiently large motional resistance, the real parts of $S_{21}$, H(F), and $50*Y_{21}$ are reasonably interchangeable with only moderate changes in the calibration curve.

FIG. 2 shows one such embodiment as a preferred embodiment of the instrumentation circuitry for an MMQSHR. Low impedance voltage source 210 excites MMQSHR 220 whose short circuit output current is amplified by transimpedance amplifier 230. The low impedance of the voltage source and the current to voltage amplifiers render physical capacitances 111 and 112 insignificant. As a result, the ratio of the output voltage of amplifier 230 to the source voltage 210 is the transfer admittance, $Y_{21}$, of the MMQSHR times the feedback resistance, $R_F$ 231 of the amplifier. In one embodiment of the instrumentation the in-phase drive signal 210 is phase shifted 215 to obtain a quadrature signal, and the drive signals are optionally buffered 235, 240 to drive mixers 240, 245 resulting in down-converted in-phase 250 and quadrature 255 magnitude signals. As the frequency of source 210 is varied, the voltages at 250 and 255 are representative of the real and imaginary parts of $Y_{21}$, namely the transfer conductance and transfer admittance, respectively. The transfer admittance is readily curve fit to obtain the elements of the equivalent circuit of FIG. 1.a under the limit of trivially small compressional wave reflections.

Performance of the quartz-based MCF structure was still limited by piezoelectric coupling; however the limitation was scaled to higher viscosities by removal of the static capacitance from its previous location in shunt with the motional resonance to be measured. The development of lanthanum gallium silicate (LGS) and other higher coupling, quartz-like piezoelectric crystals, allowed successful devices to be demonstrated. These materials have higher acoustic impedance and a higher coupling. Higher acoustic impedance results in less sensitivity to fluid damping and higher piezoelectricity results is a lower ratio of electrical equivalent circuit motional resistance to physical damping. In 2007, J. Andle, R. Haskell, R. Sbardella, G. Morehead, M. Chap, J. Columbus and D.

Stevens, "Design, packaging and characterization of a two-port bulk wave langasite viscometer", IEEE Sensors 2007, pp. 868-871, overcoming limitation (b), above.

Since many large-scale applications are for trending (aging) of in-service fluids, the deviations from Newtonian are seen to be tolerable at 5 MHz. Prior work including K. Durdag and J. Andle, "Portable/Handheld Oil Assessment Device Project: NCMS Collaborative Agreement No: 200640-140414", Final Report, Nov. 12, 2007 (unpublished), K. Durdag and J. Andle, "Real-Time Viscosity Measurement for Condition-Based Monitoring Using Solid-State Viscosity Sensor", Tribology Transactions, 51:296-302, 2008, and Andle J., Durdag K., Chap M., Haskell R., Threaded Fluid Condition Sensor for Real-Time, On-Line and In-Line Oil Conditioning Monitoring, in Proceedings of SENSOR+TEST 2009 Conference, Nuremberg, Germany, 26-28 May 2009, Vol. II, pp. 229-234, shows good correlation within broad classes of lubricants between the "acoustic viscosity" ("AV"=ρη) measured in an oscillator-based LGS MCF sensor system and the laboratory measurements of either intrinsic viscosity (η) or kinematic viscosity (η/ρ) with a linear correlation term regarding (c) above. Nonetheless, it is still desirable to eliminate the need for correlation, as well as to measure the density and even the compressional modulus of the material.

To this end, U.S. application Ser. No. 12/780,869, filed May 15, 2010 and entitled "Improved Measurement of Fluid Parameters", provides a method of transformation of the six equivalent circuit parameters into four linearized "input parameters". Two input parameters relate to energy loss (linearized motional resistance) of the two resonant transmission paths, and two input parameters relate to frequency shift (linearized motional inductance) of the two modes.

An important feature of selected aspects of the '869 application is the utilization of actual measured motional capacitance values extracted from equivalent circuit fitting of the sensor in the reference and/or measurement state, rather than the prior art use of the ideal motional capacitance as a calculated sensitivity parameter of the motional resistance to loading. Yet another important feature is the utilization of nonlinear products of motional resistances and motional capacitances (the "RC product") at each of the selected resonances, individually extracted in the equivalent circuit fitting, as a "loss" input parameter to at least one computing function. The use of the RC product in the loss parameter linearizes the sensor response. Similarly the nonlinear product of resonant frequency, motional inductance, and motional capacitance (the "ωLC product") of the selected resonances, individually extracted in equivalent circuit fitting, may be employed as a "frequency" or "phase" input parameter to at least one computing function to optimally linearize the sensor response. It is found to be advantageous to take the difference of the RC products and ωLC products between the measurement state and the reference state. It is further found that multiplication of these differences by the unloaded/reference resonant frequency, $\omega_o$, optimally normalizes the problem. The properly normalized system allows a complex input parameter, $I_m$, to be defined for each selected $m^{th}$ resonance having anharmonic number m. The complex input parameter has a real part being the loss input parameter $L_m$, and the imaginary part being the frequency input parameter, $P_m$. By analogy and the duality principle of circuit theory, it is equally acceptable to employ the R/L ratio as a loss parameter and preferably the R/ωL ratio for normalization. This is demonstrably identical to the RC and ωRC products, respectively, and is considered identical throughout the present disclosure. Similarly, ωLC is recognized as 1/ω. Therefore, 1/ω is considered identical to the ωLC product.

Thus, in the '869 application, there is provided a method of measuring the fluid mechanical properties utilizing a resonant acoustic wave device (AWD). The method begins by measuring a reference state transfer function of the AWD at a plurality of frequencies about at least one selected resonant frequency of the AWD. Equivalent circuit parameters are extracted describing the transfer function in accordance with an equivalent circuit model. The parameters are reflective of a motional resistance, a motional inductance, and a motional capacitance, which are the equivalent circuit parameters in the preferred model. After the AWD is measured in a reference state; the AWD sensor is utilized in a loaded/measurement state by imparting to the AWD a viscoelastic load of the fluid to be measured. The transfer function of the loaded AWD is again measured at a plurality of frequencies about at least one resonant frequency. The loaded equivalent circuit parameters describing the transfer function are again extracted. After the extraction of the equivalent circuit in the measurement state and the reference state, the fluid mechanical properties are calculated by defining at least one input parameter associated with the resonant frequency comprising a nonlinear combination of the equivalent circuit parameters and defining at least one output parameter related to the fluid properties, employing at least one linearized computing function relating the at least one output parameter to the differences of the input parameters from the reference to the loaded state, and calculating output parameters. The fluid mechanical property is then calculated from the output parameters of the computing function utilizing known relationships defining the output parameter in terms of the fluid properties. A one for one correspondence exists between a computing function and the output parameter that is computed.

The computing function will typically include one or more adjustable terms, called "calibration coefficients". These coefficients may be assumed, estimated, or measured experimentally.

The balance between loss and frequency parameters is indicative of the shear viscoelastic relaxation time of the fluid. Barlow and Lamb first applied this principle to quartz sensors, in the absence of any compressional mode considerations, in their paper, "The Visco-Elastic Behaviour of Lubricating Oils under Cyclic Shearing Stress", Proc. R. Soc. Lond. A 1959 253, 52-69. This approach is expanded upon in the '869 application and also in U.S. application Ser. No. 12/780,868 filed May 15, 2010, entitled "Improved Calibration of High Frequency Fluid Phase Acoustic Sensors". These applications disclose methods of simultaneously instrumenting the sensor to obtain a radiation resistance associated with compressional wave radiation, hence a product of density, ρ, and compressional elastic modulus, κ, as well as the viscoelastic relaxation time, τ, in addition to the better known product of dynamic viscosity, η(ω), and density, ρ. The '868 application, which is incorporated herein by reference in its entirety, determines the calibration coefficients by imparting viscoelastic loads to such AWD's from a plurality of known static load conditions and measuring transfer functions of the AWD about at least one resonant frequency under those known load conditions. Initial values of the calibration coefficients are selected and then an iterative process is carried out in which an error function is determined between a selected parameter measured by the AWD, or calculated from such measurement, and a corresponding ideal parameter derived from the known calibration fluid. Once the error function is determined, the calibration coefficients are adjusted and the calculation is iterated until the error function falls to within an acceptable tolerance. Importantly, the calculation utilizes the estimated viscoelastic relaxation time of the non-Newtonian calibration fluids as measured by the AWD using the assumed calibration coefficients. The computation of the ideal parameter utilizes an estimation of the shear viscoelastic relaxation time of the fluid at the resonant frequency to estimate fluid static fluid parameters from the measured parameters and adjusting this relaxation time as dictated by the adjustments in the calibration coefficients. One result of this method allows calibration of high frequency AWD sensors for viscoelastic property measurement using fluids that are non-Newtonian at the operating frequency of the AWD and for which only static viscosity information taken under Newtonian operating conditions is available. Utilizing the actual, measured motional capacitance in a manner similar to that of the present application provides a preferred method of obtaining the viscoelastic relaxation time, which simplifies the calculation of the calibration parameters.

FIG. 3 shows the response of an MMQSHR device employing split elliptical electrodes with total length 3.5 mm, total width 2 mm, and crystal thickness 0.26 mm manufactured on Y-cut lanthanum gallium silicate (LGS). The ground plane surface was loaded with test fluids, and the change in the measured motional resistances of the first and second resonant modes from the reference states were measured at several temperatures in accordance with the prior art calculations shown supra. FIG. 3 represents an attempt to graphically provide a computing function using the frequency-normalized shear acoustic impedance. Solvay-Solexis' perfluoro-polyether, HT270, is a fluid that is reasonably Newtonian at 5.25 MHz and that has been used as a viscosity standard. It shows highly linear relationships for the first (00) mode 301 and the second (10) mode 302. The slopes of these curves are substantially different, an effect for which there is no correction mechanism in the prior art theory, prior to the '869 application, using motional resistance or frequency.

A Cannon mineral oil standard, N250, is seen to exhibit an upward curvature in the response, indicative of a relaxation time that increases with increasing viscosity (decreasing temperature). Again, the two modes 303, 304 have significant differences in sensitivity. It is not possible to reliably use this measurement to obtain the differential resistance due to compressional effects 305, 306 or to obtain reliable, repeatable, and accurate viscoelastic effect measurements because of the nonlinearities of the system.

The measured value of the compressional wave radiation may be used to correct the one-dimensional estimate of the shear (viscosity) term. Direct measurement of the motional resistance ($1/g_{max}$) or estimation using curve fitting at the two modes allows matrix methods to be employed to solve the system of equations relating the shear and compressional acoustic impedances to the change in motional resistance from the nominal air value.

In the prior art, the two observables depend on two measurands, $Z_S$ and $Z_C$, which are the tangential and compressional "acoustic impedance" values of the fluid, $(2\omega\rho\eta)^{1/2}$ and $(\rho\kappa)^{1/2}$, respectively in the Newtonian limit. A system of linear equations may be written in terms of the shear acoustic impedance and the compressional acoustic impedance. The normalized shear impedance squared is called "acoustic viscosity", expressed as "AV" with units of Pa-s-kg/m³. According to the '125 application, a simple relationship can be provided for as:

$$\begin{bmatrix} R_S - R_{S0} \\ R_A - R_{A0} \end{bmatrix} = \begin{bmatrix} K_{ST} & K_{SC} \\ K_{AT} & K_{AC} \end{bmatrix} \begin{bmatrix} Z_S \\ Z_C \end{bmatrix},$$

where $R_{S0}$ and $R_{A0}$ are the symmetric and anti-symmetric resistances in air, respectively. In keeping with the '869 application, the symmetric mode is mode 0 and the antisymmetric mode is mode 1. The constants $K_{ST}$, $K_{SC}$, $K_{AT}$ and $K_{AC}$ relate $\Delta R_S$ and $\Delta R_A$ to $Z_T$ and $Z_C$. Inverting this relationship obtains a so-called computing function that would provide the acoustic impedances of the shear and compressional waves from the two measured motional resistances. The math assumes linear loading of the acoustic transmission line which requires $\rho\kappa \ll \rho_S C_{22}$ and $2\omega\eta\rho \ll \rho_S C_{66}$ where subscript S denotes the substrate density.

Knowing the two resistance values in air and in the fluid and knowing the matrix of parameters provides a system of linear equations according to the '125 application. The system of equations not only obtains the density-viscosity product as $Z_S^2$, but also compensates residual measurement errors due to unreflected compressional wave radiation provided that the determinant of the coefficient matrix is non-zero. Finally, additional information on the value of the compressional impedance squared gives the elasticity-density product, $\rho\kappa$. Frequently $K_{ST} \sim K_{AT}$ since both modes have comparable energy trapping profiles and shear wave components.

Therefore, the requirement for measuring density-elasticity (compressional impedance) is that $K_{AC} \neq K_{SC}$. This is reasonably ensured using a thickness shear (X-propagating) coupled resonator as opposed to a thickness twist (Z-propagating) coupled resonator with thickness field excitation and by having good energy trapping. Thickness twist anharmonics are desired in certain lateral field coupled resonators. For an ideal resonator, having one half wavelength of energy trapping across the diameter of the resonator for the symmetric mode and a full wavelength for the anti-symmetric mode, there is a four to one ratio of these terms. Evanescent decay beyond the energy trapping region decreases the ratio.

The changing $U_x(x)$ will result in different anharmonics having different sensitivity to compressional radiation but similar sensitivity to viscous loading as seen in FIGS. 3 and 4. This sensitivity arises from the ratio of compressional displacements to shear displacements, which is known from energy trapping considerations. The square of this ratio is denoted as $\theta_m$ for the $m^{th}$ anharmonic herein.

The solutions for the change of motional resistance 117, 120 due to fluid loading are all linearized by the real motional capacitance measured for the mode in the '869 and '869 applications. Mode shapes that are not consistent with the one dimensional model will result in very substantial changes of the sensitivity slope itself. This is compensated in these applications in the absence of compressional ripple.

FIG. 4 shows the measured response of the same MMQSHR device as depicted in FIG. 3, under the same conditions, however the improved response is obtained utilizing techniques disclosed in the '869 application. The change in the product of the measured motional capacitance and measured motional resistances ($\Delta RC$) of the first and second resonant modes from the reference states were employed as the input parameter for two resonances. FIG. 4 provides a graphical representation of a computing function to obtain the frequency-normalized shear acoustic impedance, $(\rho\eta)^{1/2}$ as the output parameter relative to the resistance-capacitance product as measured under Newtonian conditions, e.g. using an Anton-Parr SVM-3000. HT270 is a Newtonian viscosity standard and shows highly linear relationships for both transmission paths.

The slopes of these curves are substantially identical, demonstrating the efficacy of linearizing the input parameter through multiplication of the measured motional resistance by the measured motional capacitance. The example output parameter is suitable only for Newtonian fluids and presents a nonlinear computing function for other fluids. The additive effects of compressional radiation 405 and 406 are clearly visible. Mineral oil standard, N250, is seen to exhibit an upward curvature in the response, indicative of a non-Newtonian relaxation time that increases with increasing viscosity (decreasing temperature). Again, the two modes 403, 404 have significantly identical curvature and track well, allowing other processes such as Maxwellian viscoelasticity and compressional wave radiation to be clearly observed.

When fluids are Newtonian, the added motional resistance 117, 120 is equal to the product of the resonant radian frequency and the added motional inductance 115, 118. It is often stated that a TSM sensor cannot measure fluids beyond this range and that low frequency tuning fork resonators are desirable. However, the fundamentals of Maxwellian and Kelvin-Voigt pseudo-plastic fluid analysis using a TSM resonator and the extraction of the viscosity in the limit of low frequency, called the static viscosity herein, are well known, as witnessed by the aforementioned 1959 work of Barlow and Lamb.

Because of the linearity introduced by the present invention it is now possible to obtain reasonable estimates of the Maxwellian viscoelastic effects while simultaneously measuring compressional mode radiation. The mechanical impedance, $Z_S$, (ratio of stress to the time derivative of strain) is given for the shear wave in the Maxwellian model as $$Z_S = R_S + jX_S = \sqrt{\frac{j\omega\rho\eta}{(1+j\omega\tau)}}$$

where $\rho$ is the fluid density, $\eta$ is the static viscosity of the fluid, $\mu$ is the clamped shear rigidity modulus of the fluid, $\tau$ is the molecular relaxation time of the fluid, equal to the ratio of the static viscosity to the clamped elastic rigidity modulus, $\gamma/\mu$, and, for Newtonian fluids, $\tau=0$.

In order to practice aspects of the invention in non-Newtonian fluids, the complex shear acoustic impedance, $Z_S$, is then squared and the non-Newtonian relaxation time constant, $\tau$, is obtained by dividing the real part of the square of the shear acoustic impedance by the product of the frequency and the imaginary part of the square of the shear acoustic impedance. The imaginary part of the square of the shear acoustic impedance, the frequency, and the time constant are then employed to obtain the static viscosity-density product and the clamped elastic rigidity modulus-density product is then obtained as the static viscosity-density product divided by the relaxation time, $$\tau = \frac{\text{Re}[Z_S^2]}{\text{Im}[Z_S^2]},$$

$$\rho\eta = \frac{\text{Im}[Z_S^2]}{\omega}(1+\omega^2\tau^2),$$

$$\rho\mu = \frac{\rho\eta}{\tau},$$

In order to assess the role of non-Newtonian relaxation time, an approximation ignoring compressional effects is given. The results for the device used to generate FIG. 4 are shown in FIG. 5 wherein the scale calibration of the shear impedance and the compressional effects were ignored. The result was obtained only when viscosity was sufficiently large to safely ignore compressional effects. For a 5.25 MHz sensor frequency, the characteristic time of the measurement, $1/\omega$, is on the order of 30 ns. HT270 at 0° C. exhibited 2.9 ns and is still quite Newtonian. The errors associated with ignoring $\omega^2\tau^2$ are 1% in this case. Meaningful Maxwellian influence is seen for the mineral oils with $\omega^2\tau^2 \sim 1$ and a 50% decrease in apparent viscosity for N250 near −25° C. at 5.25 MHz. Efforts to separate the relaxation time effects and the compressional radiation effects have been hampered by compressional wave reflections.

The example operating frequency of 5.25 MHz results in a characteristic time of approximately 30 ns. Operation between an approximate lower limit of 1 MHz and an approximate upper limit of 25 MHz does not significantly alter the qualitative response of the sensor to mineral oils but merely shifts the specific relaxation time at which there is an observable effect. Maxwellian fluids have relaxation times ranging from about 1 ns for water to tens of nanoseconds for mineral oils to microseconds for silicones. While correlation is acceptable, a direct correspondence is preferable.

The methods offered in the Barlow and Lamb prior art and in the '125 application are limited to the case in which there is no reflection of the compressional mode energy back into the sensor from an opposing surface. It is therefore one objective to eliminate reflections and another objective to verify the quality of a measurement based on this assumption.

Prior art FIG. 6, taken from the '869 Application, illustrates the steps of measuring a transfer function (610 iterating over discrete frequency samples, 615 measuring discrete transfer function values, 620 testing if the iteration is complete, 615 obtaining the transfer function, and 630 extracting the equivalent circuit through one of many available curve fitting methods) for the reference state 605 and repeating these steps 655 in a loaded state 650. It also discloses determining input loss parameters 660 and/or input frequency parameters 665 and calculating output parameters 670 corresponding to the calibrated loaded state of the device. Finally, it discloses the calculation of relaxation time 675, dynamic viscosity-density product 678, static viscosity-density product 680, dynamic rigidity-density product 682, clamped rigidity-density product 685 and compressional elasticity-density product 690. It is noteworthy that the step of extracting the actual fluid properties requires independent knowledge of the density, which is a parameter of interest in its own right. It is also notable that the selection of the equivalent circuit of FIG. 1.*b* and the selection of only four input parameters restricts the '869 Application to certain operational conditions with regards to the reflection of radiated compressional energy back into the device. While the '869 Application offers a means of estimating the fluid compressional impedance in a finite cell and of determining the compressional elasticity-density product, there is needed a better method of implementing the computing function 670 employing additional input parameters or of overcoming the reflections in the first place.

The '869 application provides for the analysis and instrumentation of AWD resonant sensors having reflected compressional waves, provided the path length of the reflections is sufficiently short to allow the use of a lumped element model.

Judicious installation and design of sensor packaging may overcome reflected compressional wave issues to within a reasonable limit of accuracy sufficient for a trending analysis and asset management tool. However, the miniaturization inherent to increasingly higher operating pressures and the integration of additional sensing structures further complicates the compressional wave effect. Efforts to mitigate the reflections in a multi-measurand sensor are reported by J. Andle, R. Haskell and M. Chap, "Electrically Isolated Thickness Shear Mode Liquid Phase Sensor for High Pressure Environments", 2008 IEEE Ultrasonics Symposium, pp. 1128-1133, included in whole in U.S. Provisional Patent Application, 61/243,685 filed Sep. 18, 2009, from which the present application derives.

The mitigation resulted in a relatively constant motional resistance term due to viscosity that was approximately equal for the multiple modes and another motional resistance term that increased with increasing mode number in answer to limitation (d) above. The methods reviewed above also treat this case, allowing an MMQSHR to simultaneously measure the viscosity-density product, the compressional modulus-density product, and the viscoelastic relaxation time in the absence of reflected compressional mode energy. Careful installation and operation of the sensors allows these conditions to be met; however, the attendant restrictions are too burdensome on end users. Therefore, while the prior art has also addressed limitation (e) above to a limited degree, a better solution is desired.

FIG. 7 shows a measurement of viscosity-density product in accordance with U.S. application Ser. No. 12/780,869 for a measurement set with ("Reflective Fixture—REF") significant compressional reflections 701 and without ("Antireflective Fixture—AR") 702 significant compressional reflections, as described in the present invention. The reflective fixture employed a flat, parallel surface opposite the sensor while the antireflective surface comprised a conically tapered surface intended to scatter the reflections. The reflection signal's phase is a function of temperature due to the variations of phase velocity with temperature in the fluid.

The reflected signal causes an additional loss term at the points of destructive interference that are misinterpreted as additional viscosity. At the points of constructive interference the radiated energy is all returned, and the result is equivalent to having no radiated compressional energy in the first place. It is clear that the prior art method is incapable of tolerating significant degrees of compressional reflection. While the antireflective fixture measurement 702 of FIG. 7 shows considerably less ripple than the reflective fixture, it is still not a perfect example of anti-reflective fixturing. Furthermore, some reflection existed in the calibration fixture and is therefore permanently factored into the sensor response.

The overall curve of viscosity vs. temperature shows the unwanted influence of the reflections. However, in any single measurement of the fluid at any given temperature, it is not possible to tell with any degree of certainty whether or not the data is corrupted by the value of the measurement itself. It is only apparent that compressional reflections are significant when viewing the data as a whole.

SUMMARY OF THE INVENTION

The present invention discloses multi-measurand device structures that control the reflection of radiated compressional energy back into the piezoelectric sensing element. The present invention also discloses methods of instrumentation that detect, compensate, or utilize the reflection of compressional energy. Note that in embodiments, the fluid is conductive, serving as a ground electrode.

A method for simultaneous determination of physical properties of a fluid utilizing an acoustic wave device (AWD) sensor having at least two resonant modes, said modes comprising predominantly horizontally polarized shear waves, comprising the steps of: measuring a transfer function of said AWD sensor over a frequency range of interest about at least two resonant frequencies corresponding to said at least two resonant modes; decomposing said transfer function into basis functions, each of said basis functions being descriptive of a specific resonance of said AWD sensor; and deriving said physical properties of said fluid from coefficients of said basis functions describing said transfer function of said AWD sensor, wherein at least one of said basis functions is further descriptive of finite-geometry fluid resonance, and wherein said at least one of said basis functions incorporates a frequency dependence of said transfer function deviating from a lumped element equivalent circuit.

A method comprising: decomposing said measured transfer function into basis functions describing ideal resonances in absence of reflections; obtaining error function about a first resonance, being a deviation between measured data and sum of said basis functions, then modeling said error function as a first oscillatory function; refitting said measured transfer function to a first basis function of a first resonance after subtracting said first oscillatory function from measured data; obtaining error functions about additional resonances, being differences between said measured data and said sum of said basis functions, then modeling said error functions as additional oscillatory functions; refitting said measured transfer function to additional basis functions of said additional resonances after subtracting said additional oscillatory functions from said measured data in each frequency interval about said additional resonances; evaluating residual error; repeating said steps of obtaining an error function about a first resonance, refitting error-compensated first resonance to a basis function, obtaining an error function about each of additional resonances, again refitting each of said error-compensated additional resonances to additional basis functions, and evaluating until said error is minimized; and obtaining basis functions descriptive of each selected resonant mode of said transfer function compensated for errors from reflections.

A method comprising: expressing at least one of said basis functions as sum of a series resonance basis function and a transmission line basis function, estimating basis functions from intervals of a transfer function corresponding to frequency ranges about resonant frequencies of said at least two modes, ignoring transmission line effects on first iteration; partitioning basis function of first mode resonance into terms associated with a first ideal R-L-C resonance and a first series transmission line; partitioning basis function of additional mode resonances into terms associated with additional ideal R-L-C resonances and additional series transmission lines; repeating said steps of estimating, partitioning said basis function of said first mode resonance, and partitioning said basis function of said additional mode resonances until remaining error is minimized; and determining parameters from ideal resonances of said at least two modes, and from transmission line of at least one mode, said parameters reflective of said physical properties of said fluid.

A method comprising: determining compressional wave velocity of said fluid from periodicity of said oscillatory functions knowing separation distance (H).

A method comprising: ignoring said oscillatory functions and, employing coefficients of said basis functions to obtain input parameters to a computing function, outputs of which are representative of said physical properties of said fluid, wherein said input parameters are compensated for distortions of ripple.

A method further wherein said basis functions employed are sufficiently accurate to incorporate influence of fluid resonances, further comprising: decomposing a compensated transfer function comprising a sum of said basis functions into a sum of new basis functions, each of said new basis functions being descriptive of a specific resonance of said AWD; deriving said physical properties of said fluid from coefficients of said new basis functions of said AWD sensor; wherein at least one new basis function is further descriptive of said finite-geometry fluid resonance; wherein said at least one basis function incorporates a frequency dependence of said transfer function deviating from said lumped element equivalent circuit; further comprising: expressing at least one of said new basis functions as sum of a series resonance basis function and a transmission line basis function; estimating said new basis functions from the intervals of the said compensated transfer function corresponding to frequency ranges about resonant frequencies of SAID at least two modes, ignoring transmission line effects on first iteration; partitioning said new basis function of said first mode resonance into terms associated with a first ideal R-L-C resonance and a first series transmission line; partitioning said new basis function of said additional mode resonances into terms associated with additional ideal R-L-C resonances and additional series transmission lines; repeating said steps of estimating, partitioning said basis function of said first mode resonance, and partitioning SAID basis function of SAID additional mode resonances until remaining error is minimized; and determining parameters from ideal resonances of said at least two modes, and from transmission line of at least one mode, said parameters reflective of said fluid properties.

A method further comprising: decomposing said transfer function into families of at least one basis function, each of said families being descriptive of a specific resonance of said AWD, and each said transfer function within said family being descriptive of a fluid-device interaction for said resonance.

A method wherein different basis functions are employed on at least two successive iterations, producing a final decomposition.

A method wherein different new basis functions are employed on at least two successive iterations, producing a final decomposition.

A method wherein employing said coefficients of said basis functions to obtain input parameters to a computing function, outputs of which are representative of said physical properties of said fluid, comprises: wherein at least two of said input parameters are loss parameters, wherein at least two of said input parameters are frequency parameters, wherein at least one of said input parameters is a function of motional capacitance of a first resonance, said function being linearly independent of other input parameters, and wherein at least one of said input parameters is a function of motional capacitance of a second resonance, said function being linearly independent of said other input parameters.

An acoustic wave device (AWD) sensor for simultaneous determination of fluid properties, said device comprising: at least one solid structure opposite a surface of said AWD, defining finite extents of a fluid to be measured, said structure being anti-reflective to compressional waves propagating away from said surface of said AWD, preventing reflection of compressional waves that would interact with said AWD, thereby altering response of said AWD, and allowing dual mode viscosity sensor responses to be utilized for measurement of said fluid properties and correlation.

A device wherein said AWD is loaded with fluid on both surfaces and said at least one solid structure comprises solid structures opposite both surfaces of said AWD.

A device wherein said solid structure opposite a surface of said AWD comprises apertures allowing compressional waves to propagate away from said surface of said AWD unimpeded, preventing reflection of compressional waves that would interact with said AWD, thereby altering response of said AWD; said apertures allowing compressional waves to pass through said solid structure and being effectively antireflective, and allowing dual mode viscosity sensor responses to be utilized for measurement of said fluid properties and correlation.

A device wherein said solid structure opposite a surface of said AWD comprising textures, said textures randomly reflecting said compressional waves, preventing coherent reflection of said compressional waves that would interact with said AWD, thereby altering response of said AWD; said textures being effectively anti-reflective, and allowing dual mode viscosity sensor responses to be utilized for measurement of said fluid properties and correlation.

A device comprising an antireflective layer disposed upon said solid surface.

A device wherein said solid structure comprises at least one electrode of an integrated subsystem for measuring fluid electrical properties.

A device wherein said antireflective layer on said solid surface comprises one electrode of an integrated subsystem for measuring fluid electrical properties.

A device comprising antireflective supports.

A device wherein said measurement of fluid properties comprises at least one of fluid density, fluid viscosity, fluid relaxation time, fluid sound velocity, fluid acoustic attenuation, and fluid elasticity.

A multi-measurand fluid sensor system comprising: a multi-mode, quasi-shear-horizontal resonator (MMQSHR) AWD sensor; at least one proximate, effectively parallel, acoustically reflective surface; a fluid in a region between a surface of said sensor and said at least one surface; and wherein said at least one acoustically reflective surface reflects acoustic waves, said system providing for compressional wave resonances between said AWD and said acoustically reflective surface, said compressional fluid resonances coupled to said sensor quasi-shear-horizontal resonances, said compressional fluid resonances altering nominal transfer function of said sensor, said alterations being independently reflective of density of said fluid and compressional elastic modulus of said fluid.

A sensor system wherein a surface of said resonator is contoured, being functionally parallel to an acoustically reflective surface.

A sensor system wherein said at least one acoustically reflective surface comprises an electrode of a measurement cell for determining electrical properties of said fluid.

A sensor system wherein said surface of said sensor comprises an electrode of a measurement cell for determining electrical properties of said fluid.

A sensor system wherein at least one perforated solid structure is located between said surface of said AWD and said acoustically reflective surface.

A sensor system wherein said at least one perforated solid structure comprise electrodes for a measurement cell for determining electrical properties of said fluid.

A sensor system wherein said sensor is located between two mutually reflective surfaces, forming a compressional resonance therebetween.

A sensor system comprising separation value (H) selected such that, at a nominal operating temperature and fluid composition, input impedance of resonance of said fluid is purely real.

A sensor system wherein said input impedance corresponds to a minimum compressional motional resistance.

A sensor system wherein said input impedance corresponds to a maximum compressional motional resistance.

BRIEF DESCRIPTION OF THE DRAWINGS

FIG. 1 presents (a) the prior art Butterworth VanDyke equivalent circuit model of the simple TSM sensor and (b) the prior art equivalent circuit model of the MMQSHR.

FIG. 11.$b$ shows the motional resistance for the same measurement.

FIG. 19 illustrates a method of determining fluid properties from equivalent circuit parameters according to the present invention.

DETAILED DESCRIPTION

The following detailed description provides example embodiments of the presently claimed invention with references to the accompanying drawings. The description is intended to be illustrative and not limiting the scope of the present invention. Embodiments are described in sufficient detail to enable one of ordinary skill in the art to practice the subject invention. Other embodiments may be practiced with some variations without departing from the spirit or scope of the subject invention.

The present invention includes a fusion of sensor principles with the design and operation of the various subsystems advantageously integrated. In particular, the invention relates to the integration of a thickness shear mode (TSM) or similar resonant sensor into a fluid environment having finite dimensions, preferably defined by one or more sensing structures associated with one or more integrated sensing electrodes. The preferred TSM sensor is a multi-mode, quasi-shear-horizontal resonator (MMQSHR) sensor with a proximate, effectively-parallel, acoustically-reflective surface having a fluid in the intervening region. The MMQSHR may be of the thickness field excited coupled thickness shear or coupled thickness twist modes of U.S. application Ser. No. 12/036,125, or the alternate lateral field excited linearly and circularly polarized shear modes, as disclosed in U.S. application Ser. No. 12/404,288, entitled 'Improved Lateral Excitation of Pure Shear Modes', to Andle, Haskell, and Stevens, and filed Mar. 14, 2009. The MMQSHR of either excitation may comprise a single piezoelectric sensing element, a sensing element consisting of symmetrically bonded piezoelectric substrates as disclosed in U.S. Application No. 2009/0309,453, entitled "Electro Acoustic Sensor for High Pressure Environments", to Andle, filed 20 Apr. 2006, or an asymmetric composite of a piezoelectric substrate and another material as disclosed in U.S. application Ser. No. 12/202,431, entitled "Asymmetric Composite Acoustic Wave Sensor", to Andle and Haskell, and filed 2 Sep. 2008. For the purposes of the present application these shall all be collectively referred to as resonant acoustic wave device (AWD) sensors. One or both surfaces may be loaded by a fluid, and one or both surfaces may have a corresponding reflection of compressional energy. The cases are all readily incorporated into the present disclosure through proper consideration of symmetry and various factors of 2 and are collectively disclosed and discussed as single side loading for simplicity.

Figure 2:
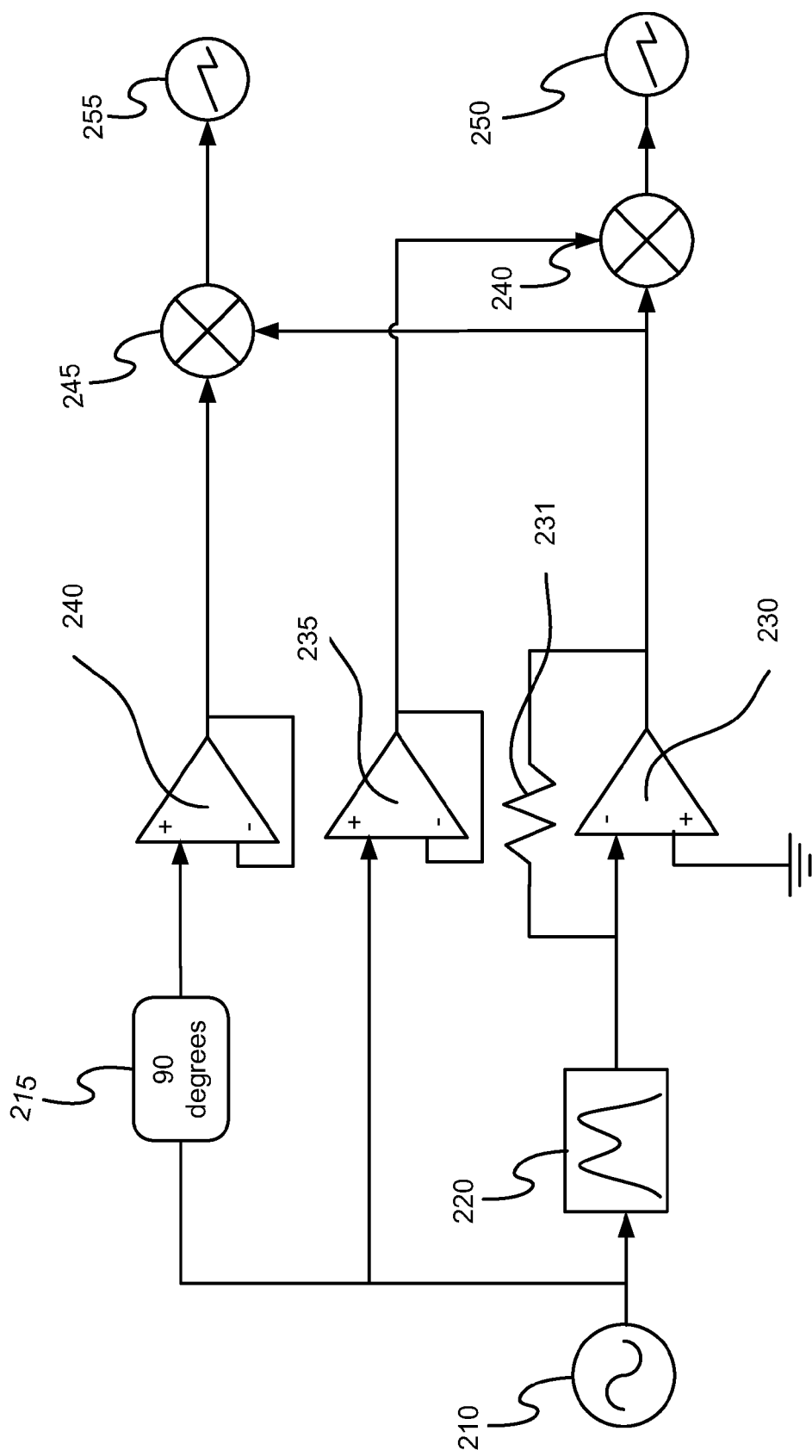
FIG. 2 presents a prior art instrumentation circuit capable of obtaining the real and imaginary parts of the transfer admittance.
Figure 3:
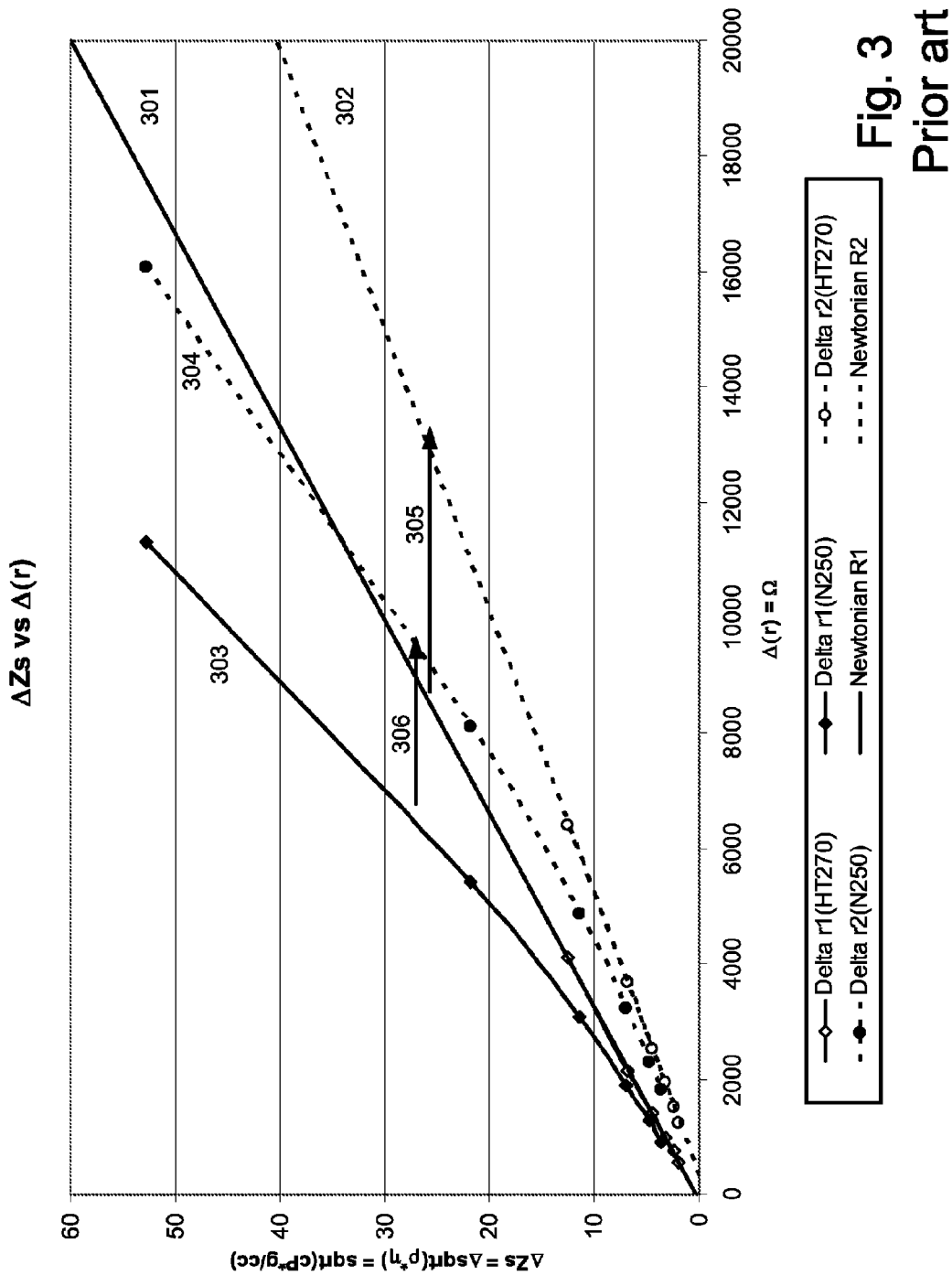
FIG. 3 is a prior art graph showing the effects of non-linearity of the sensitivity of motional resistance to fluid shear acoustic impedance as sqrt(viscoelasticity*density).
Figure 4:
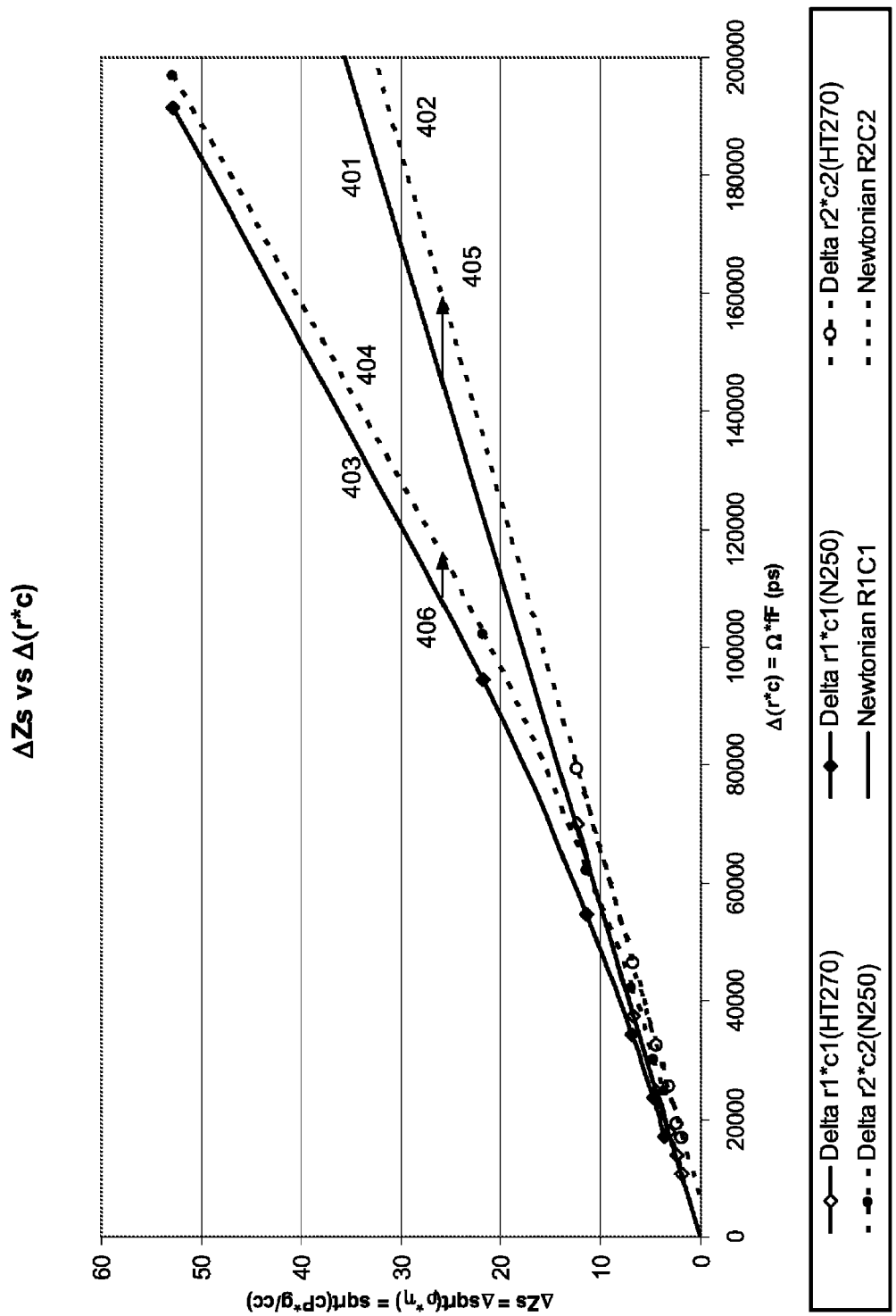
FIG. 4 presents a graph of the sensor linearized in accordance with the prior art in the absence of compressional reflections. The offset due to compressional radiation and the effects of Maxwellian relaxation times are now evident.
Figure 5:
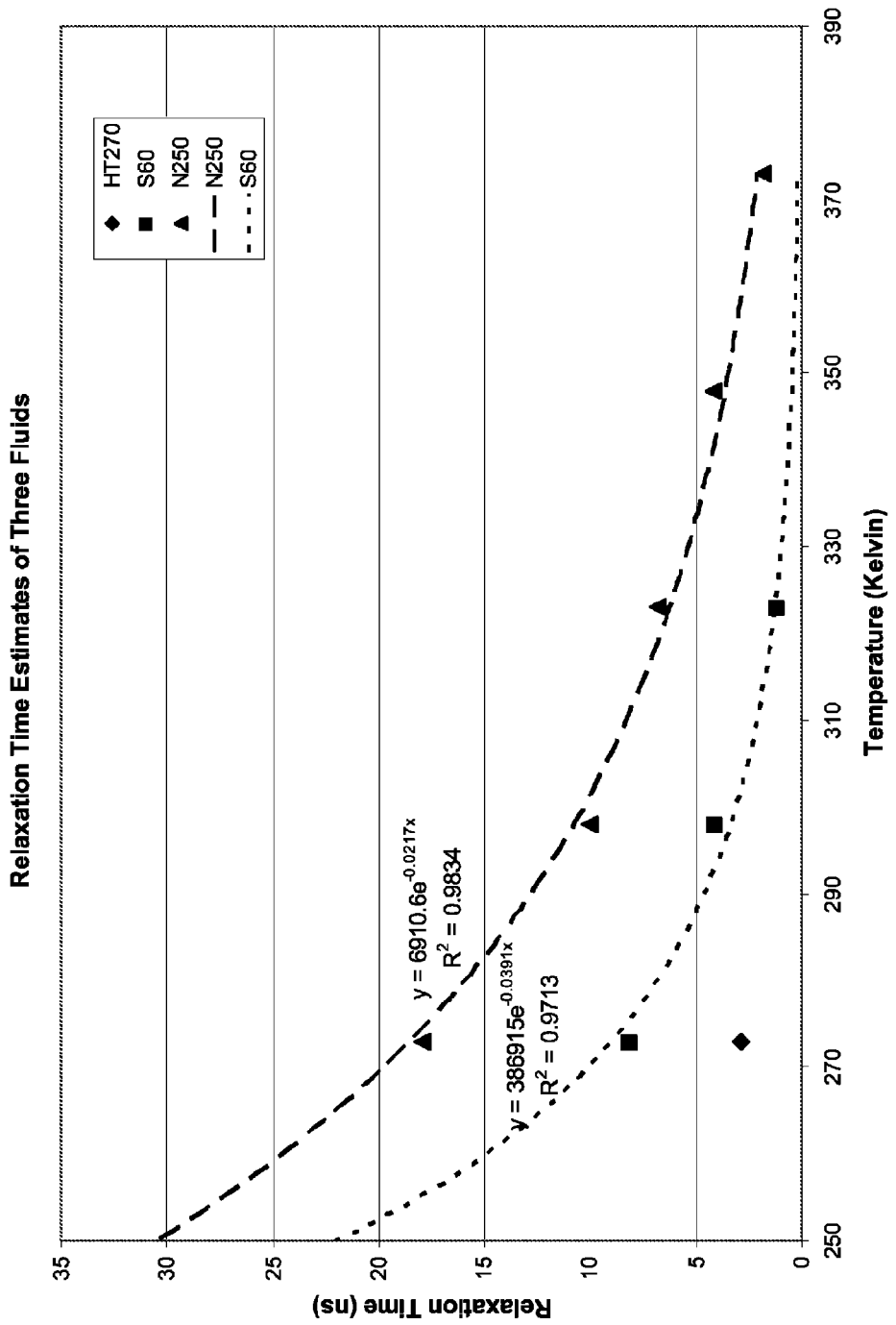
FIG. 5 is an estimate of the relaxation time in accordance with the prior art ignoring the effects of compressional radiation and reflection.
Figure 6:
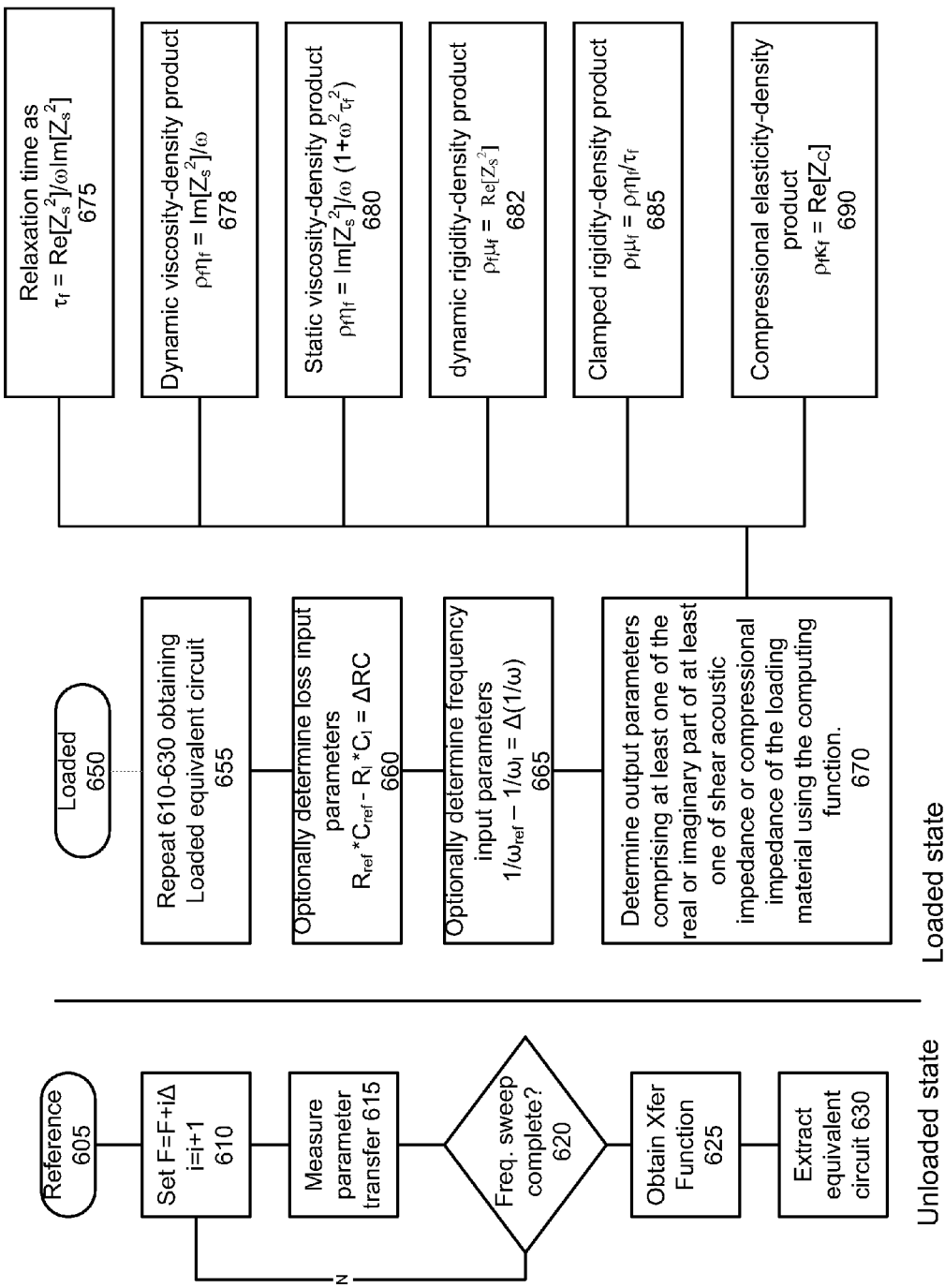
FIG. 6 illustrates a prior art method of determining fluid properties from equivalent circuit parameters according to the prior art.

In one group of embodiments, there are provided antireflective structures that allow the reflection coefficient of the incidentally radiated compressional energy to be sufficiently minimized. As seen in FIG. 6, the device itself may be antireflective but may still suffer reflections due to installation. These antireflective structures are best used with methods that detect and/or compensate the measurement result against the residual reflections. In doing so, the combination of the device and the method offer a more reliable system for measuring a physical property, such as viscoelasticity of the fluid, while reducing the constraints on installation and end use.

It is an object of the current invention to detect unwanted compressional resonances that couple to the sensor's desired resonances and to further indicate the relative quality of the sensor measurement using only the parameters already available at the time of measurement.

It is a further object of the current invention to measure and to compensate the distortions caused by unwanted compressional resonances, easing the installation and operating conditions imposed upon an end user.

In another group of embodiments, there are provided structures that produce consistent reflection coefficients of the radiated compressional energy. Providing a consistent reflection coefficient simplifies the use of methods to compensate the measurement result when it is impossible to attain antireflective opposing surfaces.

In yet another group of embodiments, there are provided structures that maximize the reflection coefficients of the radiated compressional energy and optimize the associated path length to obtain a consistent standing wave pattern and an associated functional form of the compressional wave impedance to the AWD. Providing a large reflection coefficient provides the largest possible variation between constructive and destructive interference points, allowing methods to instrument the reflected signals despite high propagation loss and relatively large path lengths between the sensor surface and the opposing reflective surface. Such an arrangement allows the instrumentation to extract additional fluid property information from the effects of the reflections.

Meanwhile, the properly designed fluid cell will have only a finite reflection coefficient on the opposing surface, eliminating a fast oscillatory error term in the fluid associated with a highly dispersive wave guiding phenomenon, discussed below. While the oscillatory error function is related to fluid properties, the associated wave guiding conditions are often too unstable to be employed in reproducible instrumentation. Nonetheless, in these cases this so-called "fast ripple" may be modeled, fit to a function, and eliminated from the remaining analysis. This allows the error source to be corrected. Finally, it is seen that only a fluid-air or a fluid-crystal-air boundary has sufficiently low reflection loss to allow this effect. Therefore, the fast ripple is available as a form of bubble detector in certain embodiments.

It is a further object of the current invention to obtain additional information on the physical properties of the fluid from the measurement of the distortions caused by the interaction of compressional wave resonances in the fluid with shear resonances in the sensor element. Such a system was disclosed in the '869 application; however the analysis therein is provided in terms of a lumped element model. The steps required to optimize reflected waves for this purpose may not be compatible with the lumped element model. Furthermore, the '869 application did not teach specifically how to optimize the reflected waves.

To this end, there is given a device, system, and method in which the reflections are maximized and controlled such that the specific influences of the compressional resonances result in instrumentable features correlated to the elastic modulus, elastic loss coefficient, and mass density.

The preferred embodiment of the present invention provides for the instrumentation of compressional wave resonances of a fluid in contact with a resonant AWD sensor, most preferably a multi-mode, quasi-shear-horizontal resonator (MMQSHR) sensor having an integrated conductivity-dielectric sensor element pair opposite the MMQSHR sensing surface. The coupled resonances are instrumented and their properties are used to extract density and compressibility modulus information.

In some cases, such as reflections from the opposite face of a fluid cell or the integration of conductivity-dielectric (CD) measurement electrodes, the reflective surface is a byproduct of the integration and installation of the sensing elements. In other cases, the reflective surface may be deliberately introduced to provide a defined and controlled reflection condition and simplify installation.

One aspect of the current invention relates to the detection of unwanted reflected compressional wave energy and the associated distortions. In order to practice such a method, it is desirable that either there be no surface opposite the piezoelectric surface or that the opposing surface be altered to suppress reflections.

Figure 8:
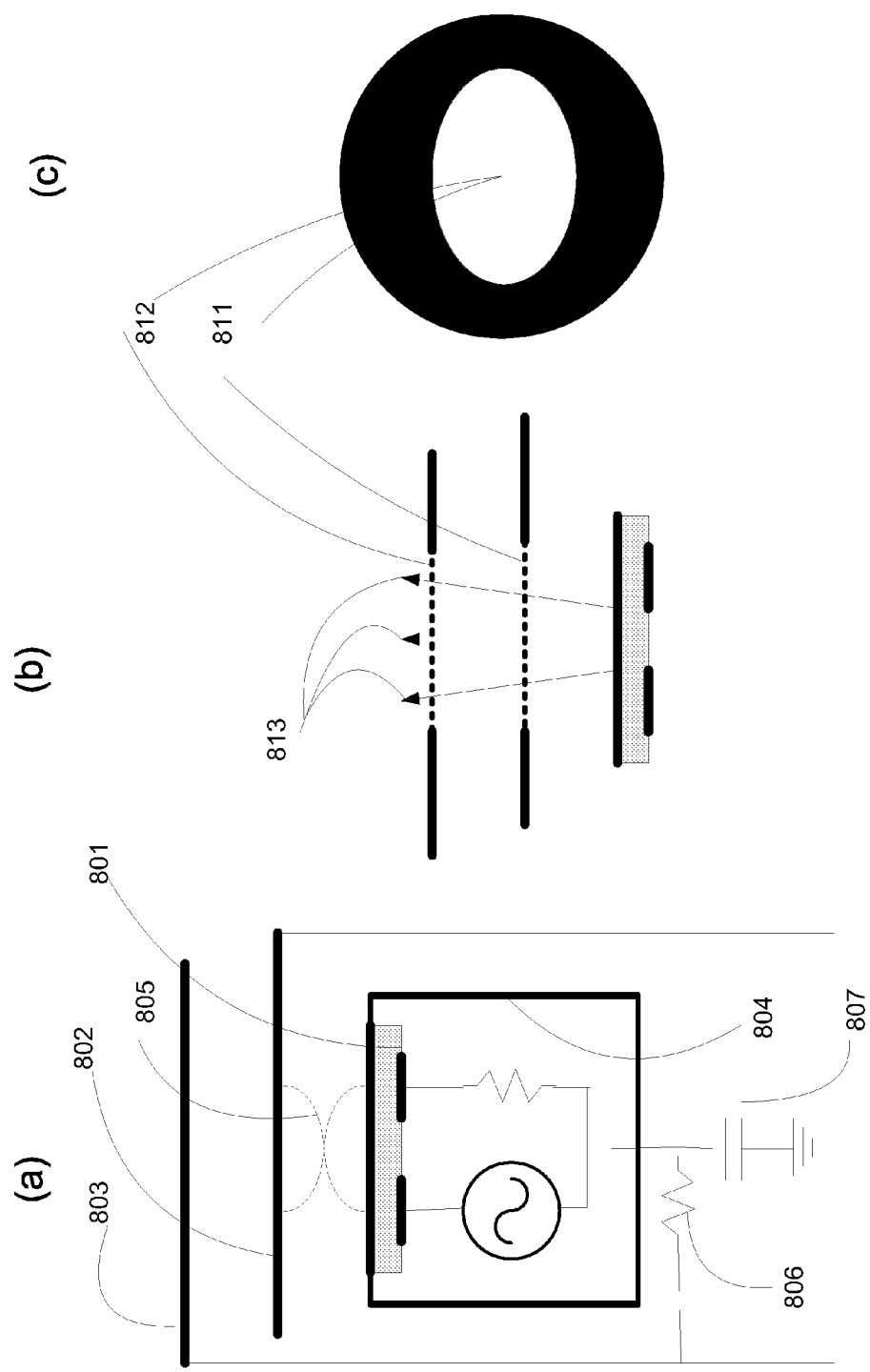
FIG. 8 illustrates (a) the integration of conductivity and dielectric (CD) measurement electrodes and the associated fluid compressional resonance, (b) the creation of an operationally antireflective electrode by perforation, and (c) a top view of the CD electrodes with an elliptical aperture to match the fundamental mode of a Y-cut LGS MMQSHR.

In one case of particular interest the proximate surface is a parallel plate electrode of a conductivity or dielectric constant (CD) measurement cell. The opposing surface reflects acoustic waves back at the MMQSHR resonator unless rendered operationally antireflective. Such antireflective electrodes allow generated compressional waves to travel through the electrodes, thereby simplifying viscosity, density, and elasticity measurements based on prior art measurement principles that are independent of the reflected signal. FIG. 8.$a$ shows an AWD sensor 801 in a sealed housing 804 with fluid loading on a single, exposed side having a reflective conductivity and dielectric (CD) probe 802, 803 proximate the sensor. A multiply-reflected compressional resonance 805 is established in the fluid between the sensor and the inner electrode 802. FIG. 8.$b$ shows the same sensor with an operationally antireflective CD probe formed by selectively removing material 811, 812 from the CD electrodes 802, 803 in order to allow radiated energy 813 to propagate away from the sensor. FIG. 8.$c$ shows a top view of electrodes 802, 803 with apertures 811, 812. FIG. 8.$a$ also shows an electrical excitation and measurement within the enclosure 804 and electrical interconnections of a driven outer electrode 803 coupled for CD measurement to the enclosure 804 of the AWD by a resistor 806 while providing RF ground to the enclosure via capacitor 807. Note that a solid structure having at least one aperture is a perforated electrode.

Figure 9:
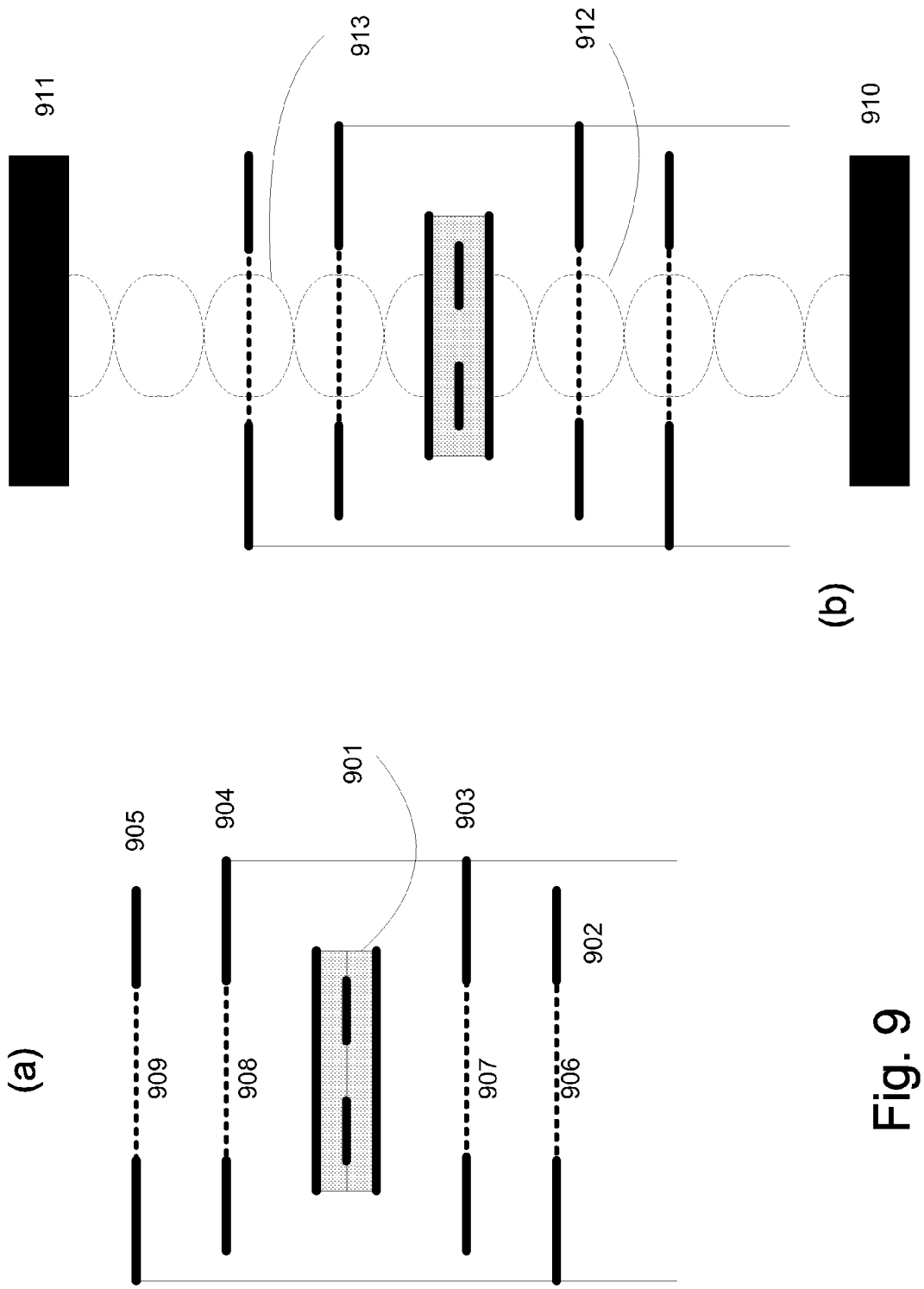
FIG. 9 illustrates (a) an alternate embodiment employing an immersible, symmetrically-bonded MMQSHR with symmetric antireflective CD cells. Also illustrated (b) is the introduction of intentional reflections at a length greater than the scale of the CD electrodes providing a defined and controlled fluid resonance.

FIG. 9.$a$ illustrates a symmetric bonded resonator with symmetric CD electrodes having operationally antireflective apertures. Composite AWD 901 is placed symmetrically between operationally antireflective CD electrodes 902, 903, 904, and 905. The entire structure is immersed, and radiated compressional waves propagate through apertures 906, 907, 908, and 909. FIG. 9.$b$ illustrates the same device with a reflective enclosure providing a controlled propagation path and reflection condition to the AWD. Composite AWD 901 and electrodes 902, 903, 904, and 905 are placed between controlled and optimally located reflectors 910, 911 to create fluid resonances 912, 913. Note that the solid surface may comprise a fluid containment cell, electrodes for fluid electrical property measurements or mechanical supports and struts for positioning the AWD, by way of non-limiting examples.

One approach to the suppression of compressional wave reflections is to remove the CD electrode material opposite the active acoustic area of the device, as illustrated in FIG. 8.$b$ and FIG. 8.$c$. This approach, having apertures or holes that can be any shape approximately related to the shape of the energy trapping of the acoustic modes; allows the radiated energy to continue, unimpeded, into the bulk of the fluid as illustrated by arrows 813. The most interesting shapes are circular or elliptical. For Y-cut LGS the energy trapping of a metal electrode is optimally elliptical for a fundamental and fifth harmonic and is optimally approximately circular at third harmonic. The remaining portion of the electrode or other proximate parallel reflective surface will be called a CD parallel ring electrode throughout the remainder of the text.

While perforation prevents strong reflection of compressional waves that would otherwise interact with the viscosity sensor surface, thus altering the device response, the transmitted wave may subsequently be reflected back through the aperture. In this manner, the perforated CD electrodes are a specific embodiment of an operationally antireflective electrode and their efficacy is limited by the propagation loss of the fluid and the installation details. Coupled with a method to validate the quality of the data by detecting undesired reflections or to compensate the reflections incidental to installation, this electrode design addresses the needs of mitigating the influence of compressional modes on the shear mode sensor.

Figure 10:
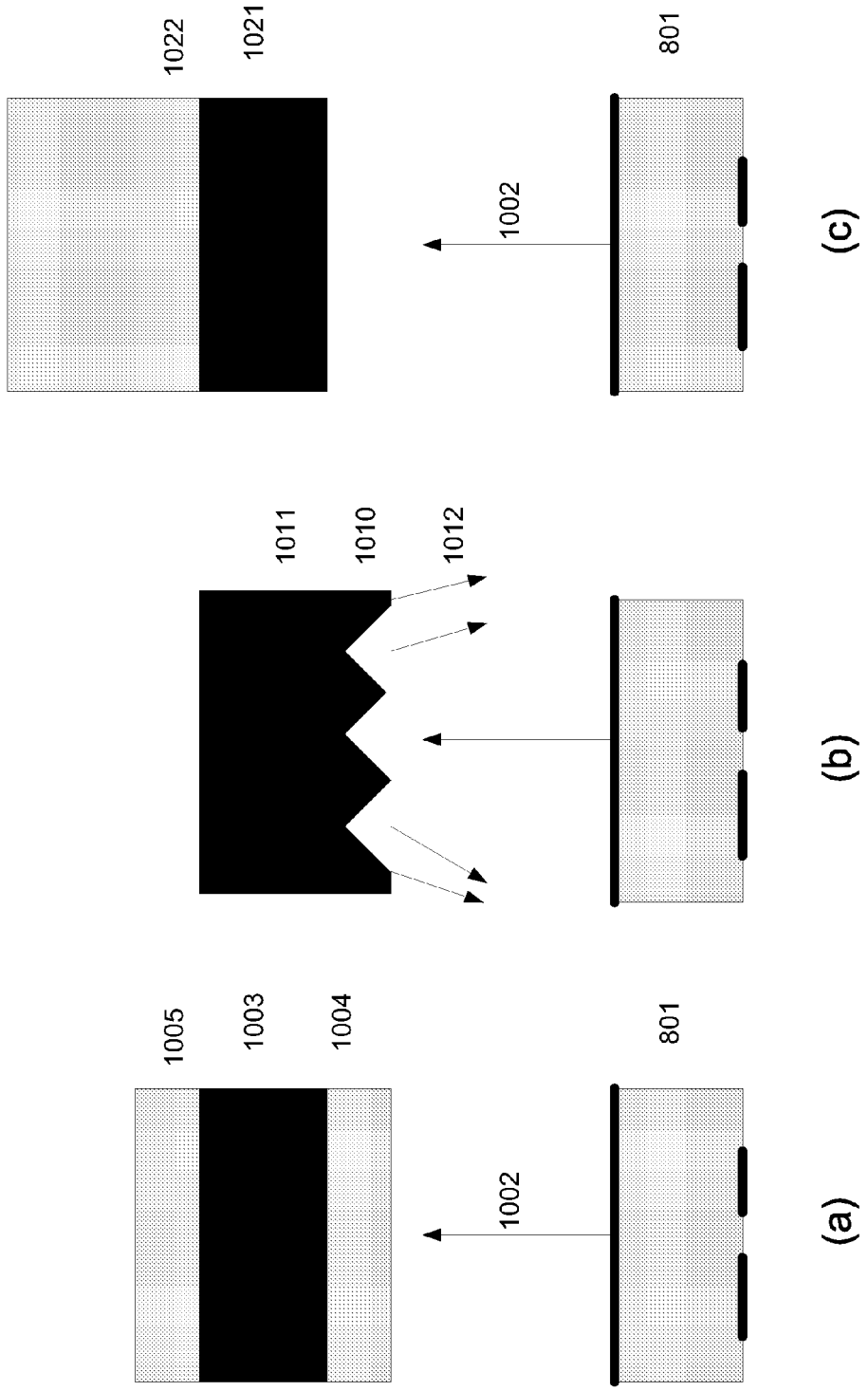
FIG. 10 illustrates alternate means of attaining an antireflective electrode or an antireflective fixture.

Several schemes to implement an antireflective electrode or surface are illustrated in FIG. 10. FIG. 10.a illustrates the sensor 801 and a normally reflective material 1003 with fluid therebetween. Antireflective coating 1004 is one quarter of an acoustic wavelength thick and has compressional acoustic impedance being approximately the geometric mean of the fluid impedance and that of the normally reflective material. For example, stainless steel has a compressional impedance of $30 \times 10^6$ and a nominal value of fluid impedance is $1.5 \times 10^6$. An antireflective layer would ideally have compressional impedance on the order of $6.7 \times 10^6$. Since even a light metal, such as aluminum, has an impedance of $17 \times 10^6$, it is clear that polymer films would be required.

In one embodiment, the reflective material is assumed to be sufficiently thick that the opposite boundary is not a source of reflections. In another embodiment the opposing surface is also coated with an antireflective coating 1005. Generally, the polycrystalline nature of most metals and the plastic losses of most polymers assure that the region 1003 will be sufficiently thick for many choices of material.

Figure 7:
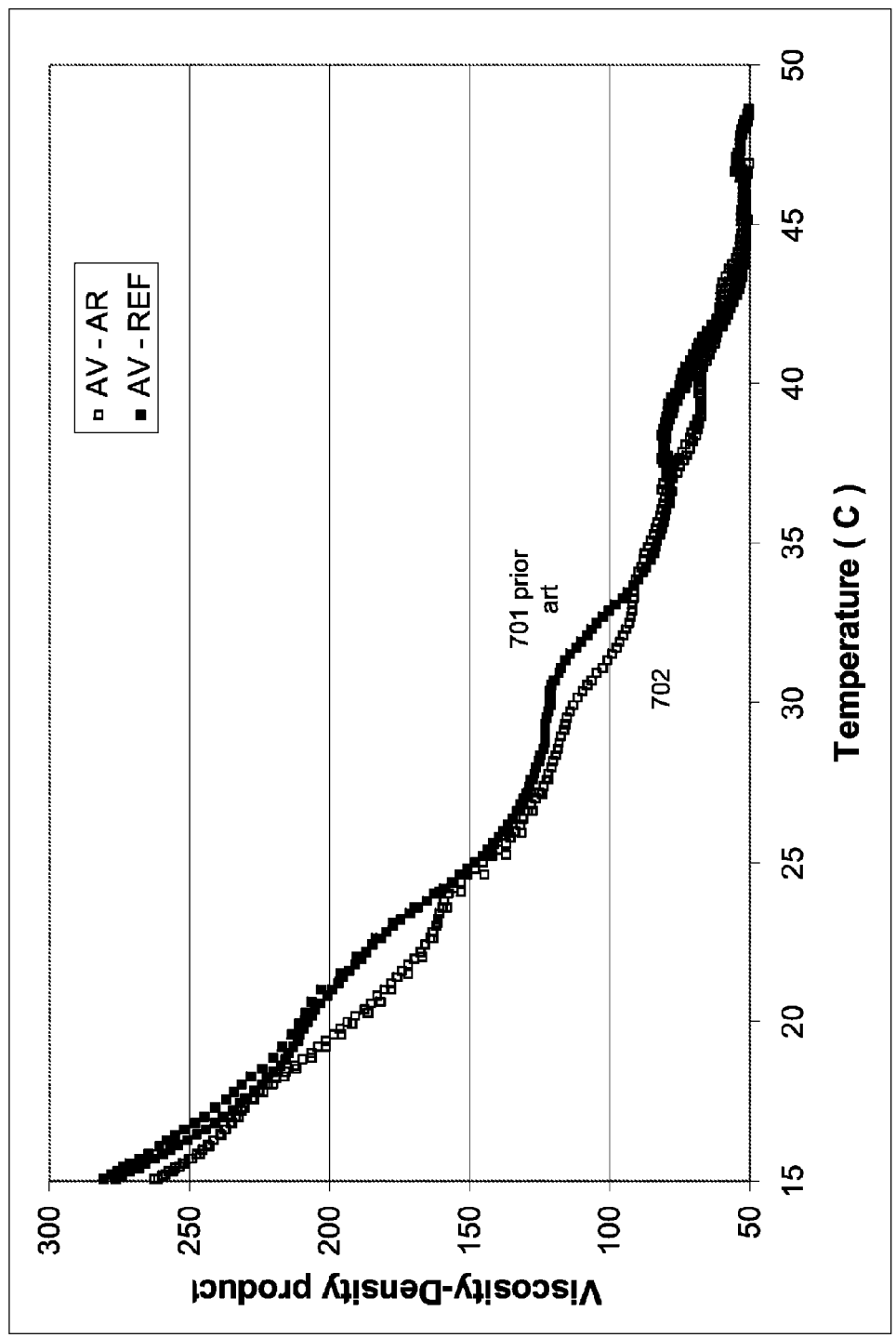
FIG. 7 compares the response of a sensor to a mineral oil measured in a prior art reflective fixture (solid squares) with the same sensor measured in a relatively antireflective fixture of the present invention (open squares).

FIG. 10.b illustrates an alternate embodiment, in which the surface 1010 of reflective media 1011 is textured so as to randomly diffract 1012 the incident acoustic wave 1002. The absence of coherent reflections is sufficient to eliminate the influence of the reflected energy. Both methods are—to some degree—dependent on wavelength of sound in the fluid and are effective only over certain ranges of operation. A limiting case of FIG. 10.b, consisting of a single, conical projection, was employed to collect the data 702 of FIG. 7.

FIG. 10.c illustrates yet another method of accomplishing this, wherein the electrode itself is the antireflective coating. The goal is to select a combination of electrode materials with acoustic impedances and phase thicknesses such that the incident signal from the fluid is not reflected. One such solution employs an electrode 1021 with thickness λ/4 having the surface opposite the fluid loaded by a damping material 1022 of impedance, $Z_D$. The electrode metal has impedance, $Z_M$, being approximately the geometric mean of the damping material impedance and the fluid impedance, $Z_F$. Since the fluids of interest may have changes in impedance between −50° C. and +150° C. of 3:1, this approach is limited to certain operating conditions. Another approach is to spatially modulate the impedance of the metal as seen by the fluid. This may be accomplished through perforations, corrugations, or patterned coatings of the CD electrodes that vary on a scale comparable to the compressional wavelength in the fluid and is a generalization of FIG. 10.b.

Collectively, schemes to render an electrode antireflective are parallel means to achieve a common goal of the present invention and the removal of material, creation of an antireflective medium, and creation of a diffractive scattering surface are but three such approaches. Any such opposing electrode shall be deemed an "antireflective electrode" and any such opposing surface shall be deemed an "antireflective surface" if the electrode or surface has been treated or coated to eliminate or substantially reduce reflections.

Regardless of the approach through which reflections are mitigated, there will always exist residual reflections of incident compressional reflections. No practical scheme of providing an antireflective environment will remain properly antireflective over large changes in fluid properties. It is understood that the operational limits related to fluid property variations might limit operating conditions over which a surface or electrode is antireflective. In situations where this distinction is germane, the electrode or surface will be deemed "operationally antireflective". The exact level of reflection coefficients that may be deemed antireflective is a matter of engineering choice. Requirements might vary from as high a reflection coefficient at −10 dB to as low a reflection coefficient as −40 dB power reflection (approximately 0.3 to 0.01 magnitude reflection). Note that primary influence of compressional reflections is to provide a transfer function that deviates from the lumped element model due to the finite phase shifts of the fluid resonance. The deviations, taken as a difference or as a ratio, from an ideal representation of the transfer function by lumped elements represents the role of transmission line or waveguide properties of the fluid resonance. Their frequency slope or dispersion offers information about the compressional sound velocity of the fluid.

In the prior art, the motional capacitance is employed to linearize the motional resistance change under fluid loading to obtain a loss parameter. It is further used to linearize the motional inductance change under fluid loading to obtain a frequency or phase parameter. However, the capacitance, itself, is not employed in the prior art. Thus, three independent pieces of information are obtained from each acoustic resonant transmission path, yet only two of these are used in the system of linear equations. One such system of equations from the '869 application presents the shear and compressional impedance of the fluid in terms of a matrix computing function taking the loss and phase parameters as $$Z_C = \sqrt{\rho\kappa}\, \frac{Z_{opp} + j\tan\!\left(\sqrt{\rho/\kappa}\,\omega H - j\alpha H\right)\sqrt{\rho\kappa}}{\sqrt{\rho\kappa} + j\tan\!\left(\sqrt{\rho/\kappa}\,\omega H - j\alpha H\right) Z_{opp}};$$

where $Z_{os}$ is the shear impedance of the sensor, $Z_{oc}$ is the compressional impedance of the sensor, the $K_{xn}$ are four calibration parameters and the loss and phase parameters, $L_{mn}$, and $P_{mn}$ of the anharmonic resonant modes of the MMQSHR are optimally normalized. The shear impedance is given in terms of the frequency, $\omega$, density, $\rho$, viscosity, $\eta$, and relaxation time, $\tau$, as $$Z_S = R_S + jX_S = \sqrt{\frac{j\omega\rho\eta}{(1 + j\omega\tau)}}$$

and the compressional acoustic impedance of a finite fluid layer with thickness H is given as $$Z_C = \sqrt{\rho\kappa}\,\frac{Z_{opp} + j\tan\!\left(\frac{\omega_0 H}{V} - j\alpha H + \frac{(\omega-\omega_0)H}{V}\right)\sqrt{\rho\kappa}}{\sqrt{\rho\kappa} + j\tan\!\left(\frac{\omega_0 H}{V} - j\alpha H + \frac{(\omega-\omega_0)H}{V}\right)Z_{opp}};$$

In the absence of compressional wave reflections, the impedance is purely real and is $\sqrt{\rho\kappa}$. With compressional reflections in a fluid with finite propagation loss, $\alpha$, height, H, phase velocity, $V=\sqrt{\kappa/\rho}$, and a characteristic impedance of the opposing material. $Z_{opp}=\sqrt{\rho_{opp}C_{22}^{opp}}$, the impedance approaches $Z_{opp}$ for very short lines, has an oscillatory but decaying behavior for moderate line lengths and asymptotically approaches $\sqrt{\rho\kappa}$ for long lines. For Newtonian fluids only the real part of $Z_s$ need be considered and the equations of the '125 application result.

The existence of an imaginary part of $Z_C$ is indicative of compressional reflections. As such, the imaginary part being non-zero is an indication that the electrode or other structure is not operationally antireflective. There is provided a means of detecting and quantifying unwanted compressional reflections.

In one aspect of the invention it is noted that the motional capacitance estimated from the curvature of the real part of the transfer admittance varies minimally and systematically with the viscoelastic and unreflected compressional loading of the sensor, whereas reflected compressional energy modulates this estimate of the motional capacitance observed from fitting the real part of the transfer function to an equivalent circuit model. There exist at least two causes of this. One is a numerical issue relating to the apparent change of curvature of the resonant peak of the transfer function when the period of the fluid resonance is close to the bandwidth of the resonance. In this case, deformations of the resonant shape may defeat certain numerically simple approaches to fitting an equivalent circuit. The second case relates to the perturbation of the resonance by the fluid resonance when the fluid resonance cannot be reasonably modeled by lumped elements. This is discussed in detail below.

Figure 11:
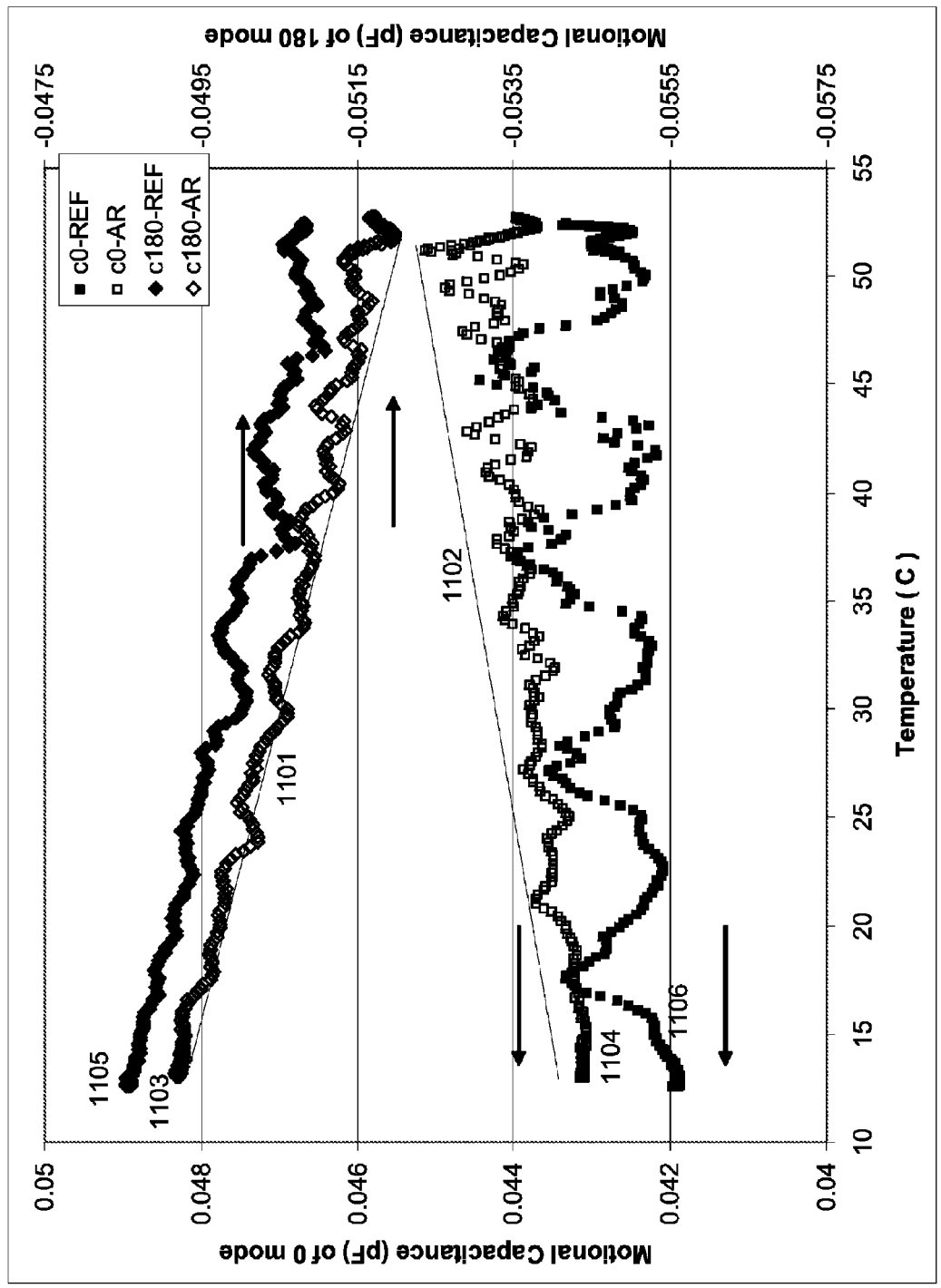
FIG. 11.$a$ illustrates the growing variability in motional capacitance, as estimated by the fitting methods using only the real part of a transfer function, with increasing compressional reflections.
Figure 11:
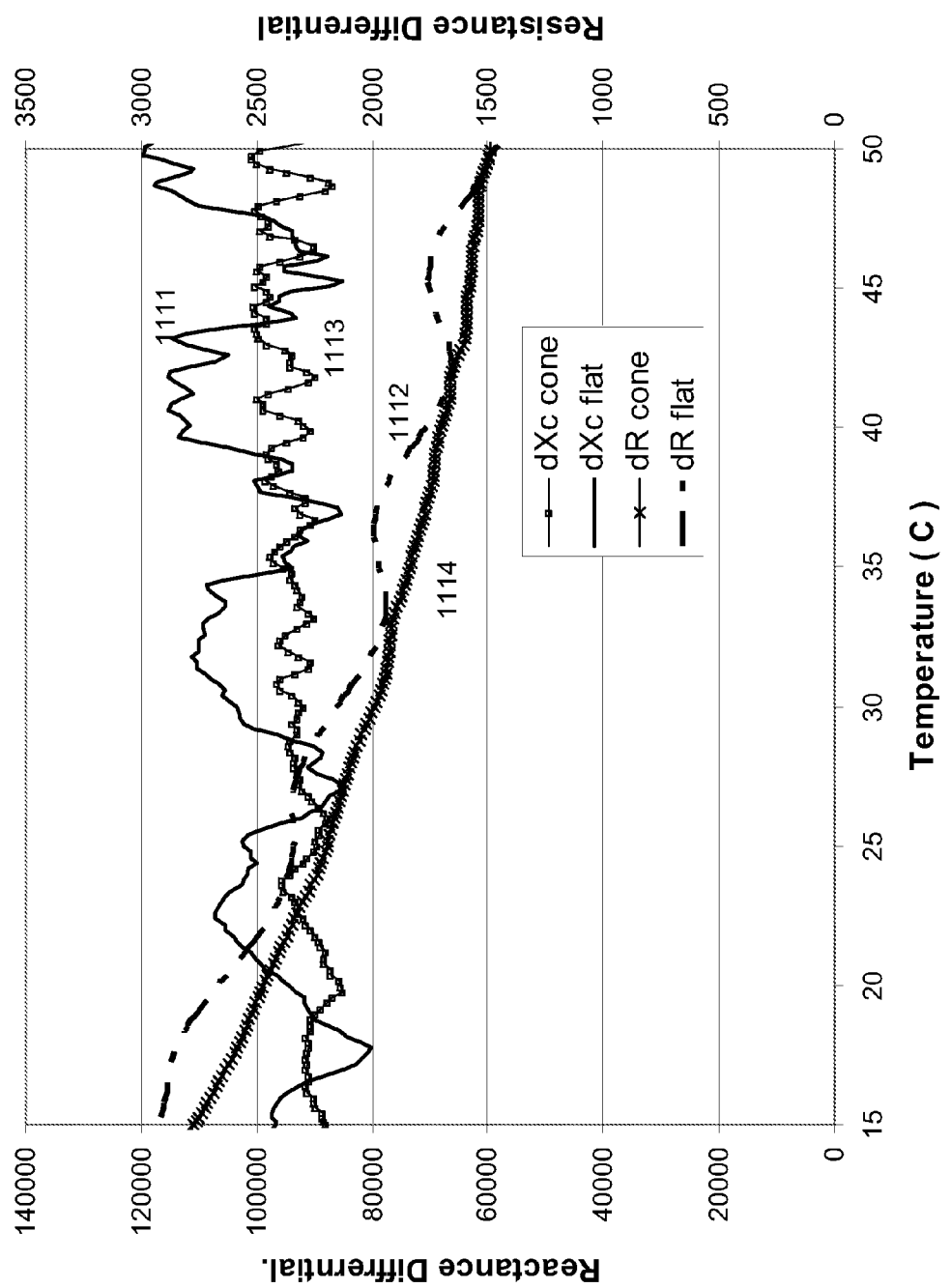

In at least one aspect of the invention, modulation of the motional capacitance from an expected result is employed to detect the quality of a fluid property measurement. FIG. 11.a shows the motional capacitance of the two modes of an MMQSHR over temperature in a mineral oil with (1103, 1105) and without (1104, 1106) mitigating the reflections of compressional energy. The mitigation is incomplete and it is known that, absent any reflections, the motional capacitance follows a well-behaved, nearly-linear temperature dependence as indicated by lines 1101 and 1102. The motional capacitance of the devices of FIG. 6 are shown with (solid symbols) and without (open symbols) intentional reflection for the 0° (squares) and 180° (diamonds) modes. In one device a flat steel surface is spaced opposite the MMQSHR while in the other a 45° conical shape is used to scatter the reflections in accordance with one embodiment of FIG. 9.b. It is seen that the motional capacitance deviates dramatically from the baseline value. The deviations are significantly worse for the 0° mode than for the 180° mode and significantly worse for the flat reflective surface than for the conical antireflective surface. It is also clear from the figures that the suppression of reflections by the simple conical taper of the surface is incomplete.

FIG. 11.b shows the difference between the mode 0 and mode 180 values of the capacitive reactance and the motional resistance. The differential capacitive reactance with the flat opposing surface 1111 and the differential resistance for the same measurement 1112 are seen to exhibit ripple from the reflectionless reactance 1113 and resistance 1114 that are out of phase with each other. Therefore, while the capacitance alone gave an inconsistent picture of the presence of reflections in FIG. 11.a, the combination of capacitive reactance and resistance differentials between the modes provides an indication under all phase conditions. With respect to the input parameters of the '869 Application, the individual motional resistances are already incorporated as the loss parameters, so the differential resistance is implicitly available to the computing functions. Taken with the differential capacitive reactance, it may be employed to detect unwanted compressional reflections. Methods explicitly using the differential capacitance, differential resistance, or both are contemplated. More importantly, the differential capacitive reactance and differential resistance of each higher order mode with respect to the zero$^{th}$ (180°) mode may be employed as an additional N−1 input parameters for an N-mode sensor. It is understood that any mode may arbitrarily be called the $0^{th}$ mode. In the present example of a dual mode sensor, there would now be five or six measured input parameters. In principle, this allows at least five fluid properties to be measured.

Figure 12:
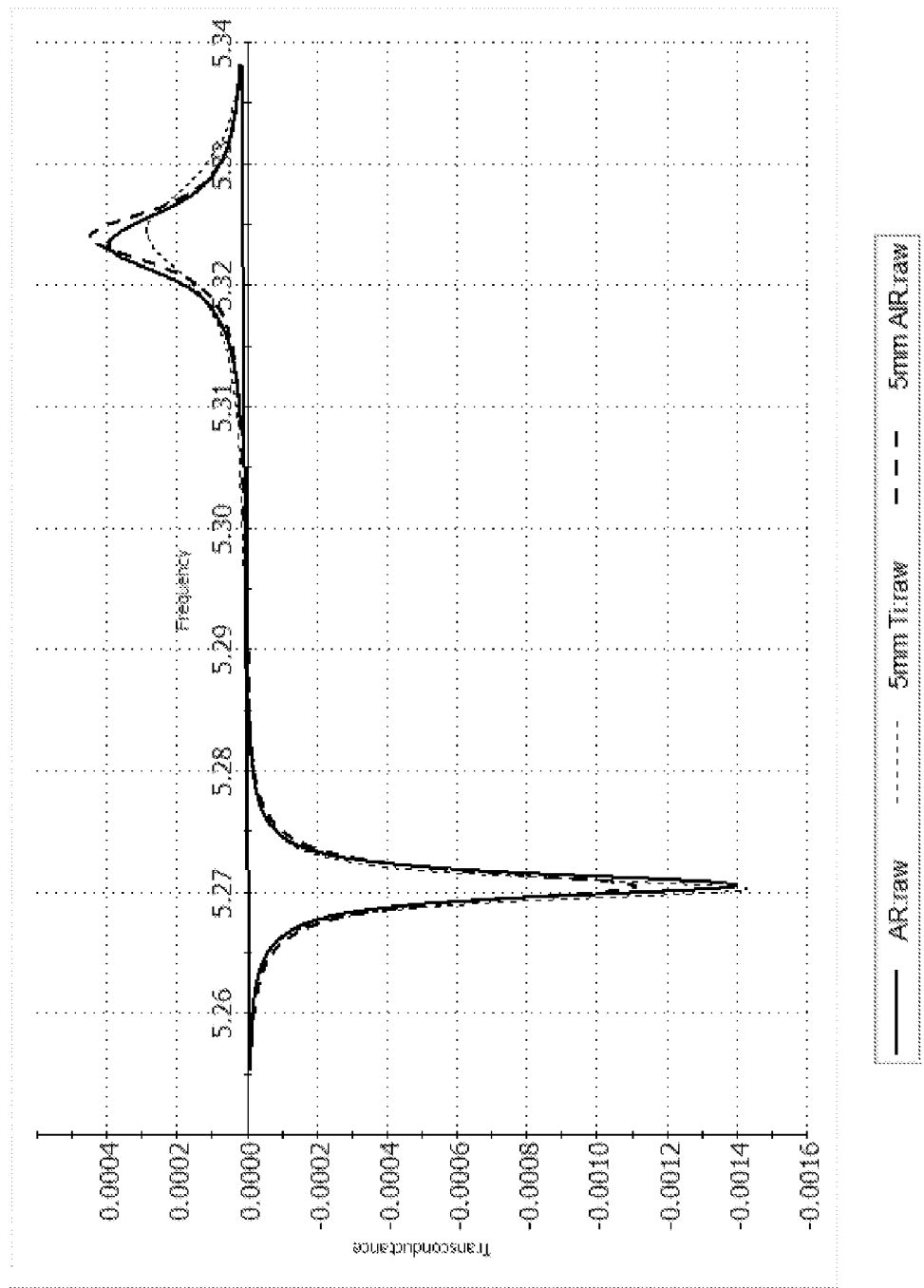
FIG. 12 illustrates the effects of slow ripple on the measured transfer functions of the MMQSHR. The baseline data with an antireflective fixture (solid line) is compared to 5 mm separation to titanium (fine dash) and air (heavy dash).

The effect of the compressional reflections is to return energy at a variable phase to the shear resonance. The effects of reflected signals on frequency and on loss were disclosed and claimed in the '869 Application. FIG. 11.a and FIG. 11.b note a change in the motional capacitance due to the reflections, separate from the frequency shift, which was not anticipated in the '869 Application. When in phase or out of phase, these reflections raise or lower the measured motional resistance, as seen in FIG. 12. Typically the decrease in motional resistance (increase in $|Re[Y_{21}]|$) is small and increases in resistance (decreases in $|Re[Y_{21}]|$) are more substantial, as seen in the figure. It is also seen that when the reflected compressional wave is constructive for the 0° mode, it is destructive for the 180° mode and vice versa, hence the differential signal is responsive to compressional energy reflected back to the sensor. It should be noted that any increase in $Y_{21}$ (decrease in resistance) is limited and cannot exceed the result of cancelling the value of the antireflective radiation resistance; however the increase in resistance may be infinite at resonance conditions and $Y_{21}$ may become zero.

Any other phase component of the reflected signal is at least partially reactive and alters either the motional inductance or capacitance, depending on the phase shift. Again, a frequency increase for the 0° mode will tend to correspond to a frequency decrease for the 180° mode and vice versa. Also notable is that the motional capacitance of the two modes is changing with the reflection, as seen in FIGS. 11.a and 11.b and as seen in the changing curvature of the modes in FIG. 12. There is seen a decrease in the magnitude of the motional capacitance and (predominantly) an increase in the motional resistance for the modes that varies cyclically with the phase of the reflected compressional wave relative to the shear resonance of the MMQSHR.

By comparing the deviation of the motional capacitance from the value in air against the other measured values, it is possible to quantify the degree of the distortions in at least some cases. The change of motional capacitance with certain viscoelastic loadings has been reported in the prior art for fluid loading by Arnau, Jiminez, and Sogorb, in their paper entitled "Thickness shear mode quartz crystals in viscoelastic fluid media", JAP 88(8), pp. 4498-4506 (2000); however they did not address reflected energy. There are also artifacts of the curve fitting process in the prior art that result in reproducible errors in calculating the motional capacitance. These systematic errors are further indicative of the reflected energy as the measured data ceases to agree with the basis functions of the resonator in anti-reflective environments.

It is seen that the additional information carried in the motional capacitance may be used to detect imbalances in the loss and frequency parameters due to compressional wave reflections. Since the results are sometimes in balance, even with reflections, the method of using the motional capacitance alone is only of limited value compared to using both the motional capacitance and the differential imbalance of the $\omega RC$ term.

The previous figures and discussions all relate to data sets with slowly-varying compressional mode distortion. The following data shall illustrate the significant influence of reflected compressional modes. The MCF's frequency response is characterized by two desired modes. The first mode is the symmetric mode, corresponding to a 180° electrical phase shift, while the second mode is the anti-symmetric mode corresponding to a 0° electrical phase shift.

The symmetric mode is very similar in mode shape to the one-port resonator. Therefore, the sensitivity of surface impedance (Zs) is dominated by $(\rho\eta)^{1/2}$ with only a small component of sensitivity to $(\rho\kappa)^{1/2}$ due to compressional wave radiation determined by its relatively flat $\cos((0\pi+\delta)x/L)$ mode shape distribution across the resonator. The compressional to shear wave ratio, $\theta_0$, is approximately $(\delta L/t)^2$ for a crystal of thickness, t, where $\delta \to 1$.

The sensitivity of the anti-symmetric mode is also dominated by $(\rho\eta)^{1/2}$. However, due to its steeper mode distribution, $\sin((\pi+\delta')x/L)$, across the surface of the resonator, it will have approximately three to four times the compressional wave radiation of the symmetric mode. The compressional to shear wave ratio, $\theta_1$, is approximately $((1+\delta')L/t)^2$ for a crystal of thickness, t. Typically $\delta'<\delta$, but the values are similar in good designs. The sensitivity ratio is approximately $$\theta_1/\theta_0 \approx ((1+\delta')/\delta)^2$$

and is determined by the device energy trapping parameters, $\delta$ and $\delta'$, which are always less than 1. The sensitivity to $Z_C$ is approximately increased by a factor of at least four over that of the symmetric mode when $\delta$ and $\delta' \to 1$. Given the elasticity of the fluid, use of data from the two modes allows the extraction of density and viscosity given that the two modes have comparable sensitivity to $Z_S$ and differentially significant sensitivity to $Z_C$. Conversely, given the density, it is possible to calculate the elasticity and viscosity.

An approach and method for a pair of single-mode resonators was proposed by Kim et al. using a singly rotated and a doubly rotated resonator pair, wherein the model estimated $\Delta(Z)$ with $Z_C=(\rho\kappa)^{1/2}$. The present invention allows a single resonator to perform the same measurement using two anharmonics but to also obtain a measure of the compressional wave fluid velocity, $V=(\kappa/\rho)^{1/2}$.

The above offers a means to detect imbalances in the measurement due to reflected compressional energy. What is desired is a method and device that will allow these reflected signals to probe the bulk of the fluid and provide additional information. In principle, since the model of FIG. 1 has six independent pieces of information, it should be possible to extract up to six fluid properties; however the acoustic impedances of the fluid always present the product of density and another parameter. Therefore, it is not possible to extract density from the equivalent circuit of FIG. 1 without knowledge of other parameters. The distortions due to reflected compressional energy over a finite path length offer the necessary data, since the phase shift of the reflected signal is related to the velocity of the sound wave in the fluid, which is $(\kappa/\rho)^{1/2}$. Having the ability to extract the sound velocity and the compressional impedance allows separation of variables and the determination of density.

It is recognized that the fluid of finite geometry represents a waveguide resonator. The simplest mode of such a resonator is a pseudo-plane wave between the two reflective faces and may be treated as a transmission line with an impedance mismatch at the opposite end. A significant observation is that the impedance at the input of the compressional wave transmission line cannot be approximated by lumped elements over an arbitrarily wide band and that the deviation from the ideal lumped element model depends on the phase term that is the product of the radian frequency and fluid thickness divided by the velocity of sound in the fluid, $\omega H/V$. The same is true of the piezoelectric sensor resonance; however over any reasonable fluid loading the deviation of the lumped element model from the more exact transmission line model is negligible. Since the fluid is typically operating in a harmonic of the fundamental resonance, the range over which lumped element models are accurate is correspondingly more limited. Under judicious design conditions, the quality factor of the resonance in the fluid will introduce measurable deviations from the lumped element equivalent model. The deviations of the transmission line from simple lumped element approximations will become evident and will be indicative of the phase velocity and/or physical length of the fluid transmission line.

Figure 13:
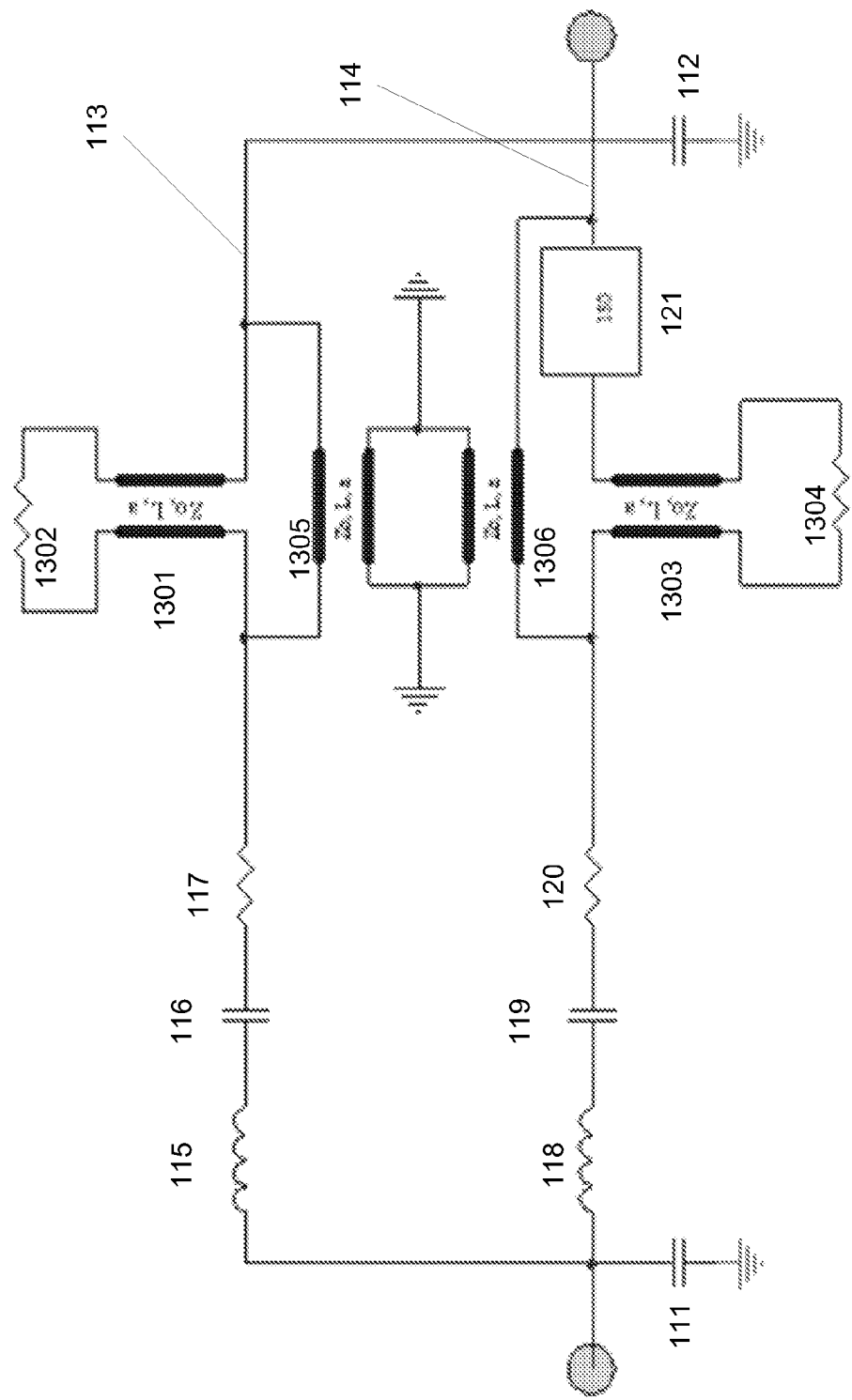
FIG. 13 is an equivalent circuit of the MMQSHR according to the present invention.

FIG. 13 presents a proposed expansion of the equivalent circuit of the MMQSHR. The model elements of FIG. 1 are repeated with their original designators. The additional features consist of two transmission lines 1301, 1303 and two terminating impedances, 1302, 1304, describing the slow resonance of the fluid and an additional two transmission lines 1305, 1306, describing the transmitted waveguide mode. The transmission lines have unique impedances and lengths, since they have unique $\theta_m$ and numbers of bounces. In practice, when compressional reflections are intentionally generated, $Z_{opp} >> Z_o$. The transmission lines are weighted by the electrical to mechanical transformation and also by the compressional to shear coupling factor.

Modeling the sensor to incorporate the effects of the fluid resonances and wave-guiding results in the circuit model in FIG. 13 by fitting the overall response to three subsystems per acoustic mode resonance. One subsystem is the series electrical resonance that is the traditional motional resonance of the resonant mode in the crystal, $Z_{m1}$, $Z_{m2}$, . . . (the "ideal resonance"). This impedance is comprised of an inductance, $L_m$, a capacitance, $C_m$, and a resistance, $R_m$. In series with these motional terms of the ideal resonance, there is embedded a series path representing the one dimensional resonance of the compressional wave in the fluid ("Series Transmission Line"). This subsystem is scaled by a transformer (not shown and implicit to the values calculated) whose turns ratio is a property of the crystal, $(\theta_m/\omega C_m(\rho_s C_{effS})^{1/2})^{1/2}$, where $\theta_m$ is the shear-to-compressional conversion, $C_m$ is the motional capacitance, $\rho_s$ is the substrate density, and $C_{effS}$ is the substrate elastic modulus of the substrate. The transformer is loaded by a transmission line describing the fluid. When $Z_{opp}=(\theta_m/\omega C_m(\rho_s C_{effS})^{1/2})(\kappa\rho)^{1/2}$ or when the line length is infinite, then the transmission line simplifies to a simple compressional radiation contribution to the motional resistance as in the prior art. Typically, $C_{effS}$ is $C_{22S}$.

Completing the circuit is a shunt path associated with fast ripple of the waveguide mode for each resonance ("Periodic Ripple Function"), which is modeled as a dispersive waveguide seen through transformers converting shear to compressional and back. The waveguide is assumed to be sufficiently lossy as to allow multiple reflections to be ignored. This fast ripple occurs only in anomalous conditions and is highly unstable. In the discussions that follow, it is assumed that this fast ripple if filtered from the data and so-called measured data is, in fact, filtered to eliminate these effects unless otherwise stated.

It can be shown that, absent the compressional reflections, the model of FIG. 1.b is reasonably accurate and may be fully described by the parallel combination of two impedances, $Z_n(\omega)$, being described by the lumped elements indicated. Decomposing the transfer admittance, $Y_{21}$, into at least two parallel $Y_n(\omega) = 1/Z_n(\omega)$ describing at least two resonant modes of the sensor, it is found that the real part of each $Y_n(\omega)$ has an inverse-parabolic form absent reflections and within a moderate frequency range. Introduction of reflections at a frequency-dependent phase distance, $\omega H/V$, distorts the parabolic form of $1/Re[Y_n]$ and injects higher coefficients to the inverse-polynomial fitting function.

In one method, the peak deconvolution proceeds by fitting the transfer function to a plurality of ideal resonances. In a preferred embodiment, the transfer function is the real part of the transfer admittance and the ideal resonance basis functions are inverse-parabolic fits of the real part of the admittance. Inverse parabolic fits are attractive as they represent the natural description of a series R-L-C ideal resonance close to the resonant frequency and allow analytical fitting. Fitting separates the at least two resonant transmission functions in a series decomposition. One variant of the method further requires knowledge of the imaginary parts of $Y_{21}$, which may also be fit or may be obtained as Hilbert Transforms of the real part or obtained from the equivalent circuits corresponding to the inverse parabolic fits.

The ideal resonances are then used only to compensate the measured transfer function in one frequency interval for the ideal overlap of the other mode resonances. For each mode there is then computed a $Y'_n(\omega)$, being the remainder of $Y_{21}$ measured minus all of the other modes' ideal resonances and all of the other modes' imaginary part fits. $Y'_n$ is inverted to obtain $Z'_n(\omega)$ and—absent reflections—the real part is a constant being the motional resistance. With reflections, the real part of the resonant transmission line input impedance is seen in the difference between the measured transfer function and the decomposition.

Figure 14:
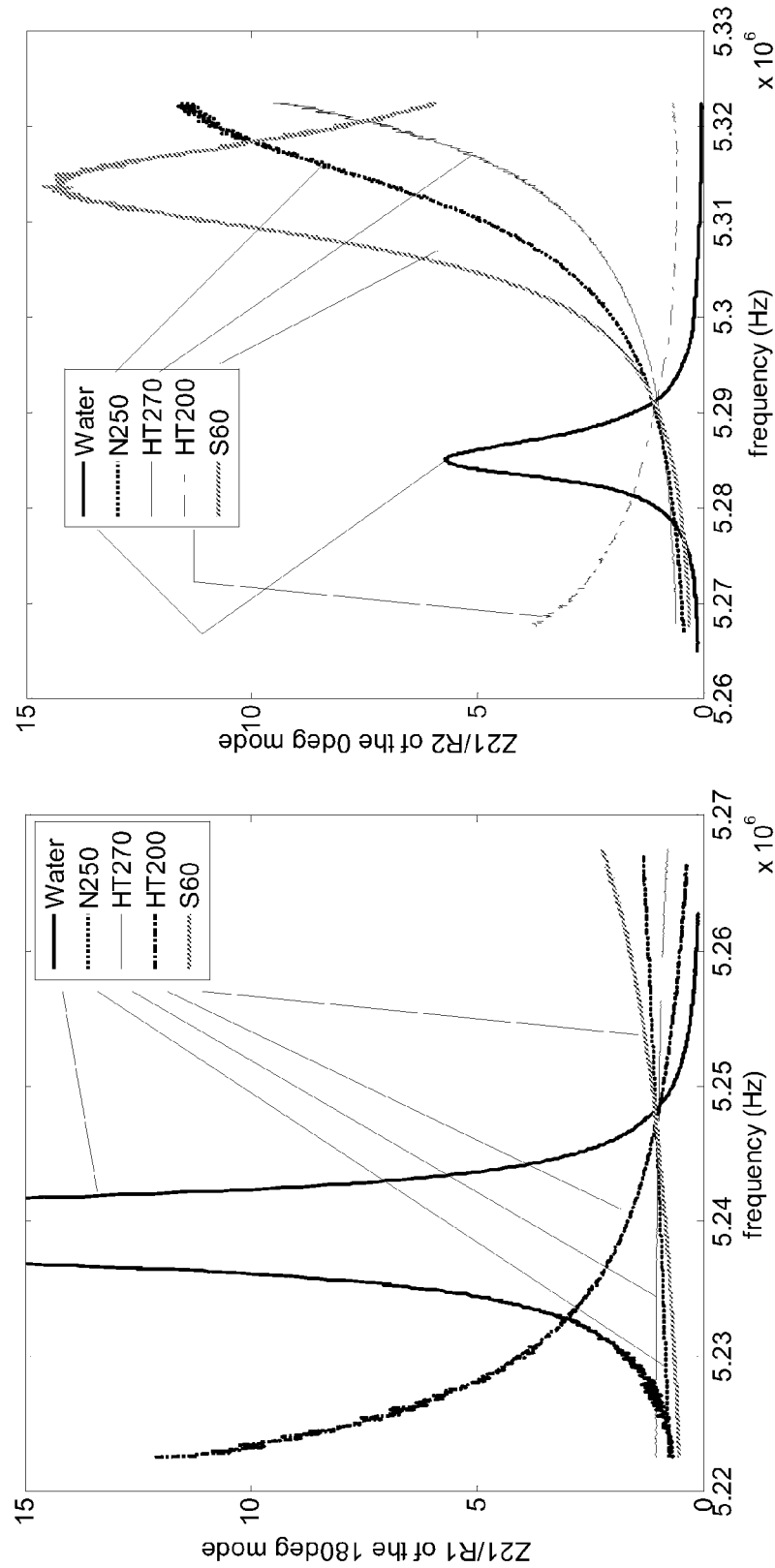
FIG. 14 shows the distortions of the frequency dependent motional resistance due to the reflections.

The value of $Re[Z'_n]$ is normalized to the ideal result of the parabolic fit, $R_n$, for the 180° (n=0) and 0° (n=1) modes in FIG. 14. While both modes have compressional mode content, the 0° mode is typically used in the MMQSHR specifically because of its higher content of compressional energy. The real part of the impedance is seen to be the constant resistance plus a term derived from a lossy, terminated, transmission line. The constant term, $R_n$, comprises one term due to viscoelastic losses, $R_{\eta n}$, and another due to the unreflected radiation of compressional waves, $R_{\kappa n}$. The latter term is $(\theta_m \sqrt{\rho\kappa}/\omega C_m(\rho_S C_{effS})^{1/2})^{1/2}$, and already accounts for the characteristic impedance of the transmission line.

The real part of the input impedance of a fluid waveguide terminated in a mismatched impedance is given in terms of the acoustic impedance of the opposing surface, $Z_{opp}$, the acoustic impedance of the fluid, $\sqrt{\rho\kappa}$, the propagation loss term, $\alpha$, the nominal phase length, $\omega_o H/V$, and the phase dispersion, $(\omega-\omega_o)H/V$. The scaling factors are $\theta_n/(\omega C_n \sqrt{\rho_S C_{effS}})$, where $\theta_n$ are the compressional transformation ratios of the modes, $C_n$ are the motional capacitances of the modes, $\rho_S$ is the substrate density, and $C_{effS}$ is the substrate effective shear elastic constant. Since $R_{\kappa n}$ already contains the characteristic impedance of the transmission line, this term must be subtracted from the line equation. Substituting for velocity, the equation is $$R = R_{\eta n} + R_{\lambda n} + \frac{\theta_n \sqrt{\rho\kappa}\left(1 - \frac{\sqrt{\rho\kappa}}{Z_{opp}}\right)}{\omega C_n \sqrt{\rho_S C_{effS}}} Re\left[\frac{1 - j\tan(\sqrt{\rho/\kappa}\,\omega H - j\alpha H)}{\frac{\sqrt{\rho\kappa}}{Z_{opp}} + j\tan(\sqrt{\rho/\kappa}\,\omega H - j\alpha H)}\right];$$

Due to the non-zero value of $\alpha$, $\kappa$ is also complex but to reasonable accuracy the imaginary part of this term may be ignored. The shape of the resistance vs. frequency is then fit to the frequency dependence of the model above by varying the density, $\rho$, the elastic modulus, $\kappa$, and the propagation loss, $\alpha$, or alternate variables reflective thereof. It is also possible to allow the opposing impedance to be a fit variable; however, the fluid cell dimension, H, must be known. As seen in FIG. 14, the deviation from a constant value has at least a sufficient curvature to be fit to $Re\{Z_{in}\}$. Therefore it is possible to extract the propagation loss, $\alpha$, the fluid impedance, $Z_o$, and the phase velocity, V, if the opposing reflector impedance, $Z_L$, and the fluid thickness, H, are known.

In an alternate method, the peak deconvolution proceeds with generalized basis function of the individual resonances to decompose the measured data into the at least two resonant transmission functions. Again, the preferred embodiment employs the real part of the transfer admittance; however other transfer functions may be employed as a matter of technical choice. The form of the basis function must be sufficient to capture the deviations from inverse-parabolic that occur due to fluid resonances.

Figure 15:
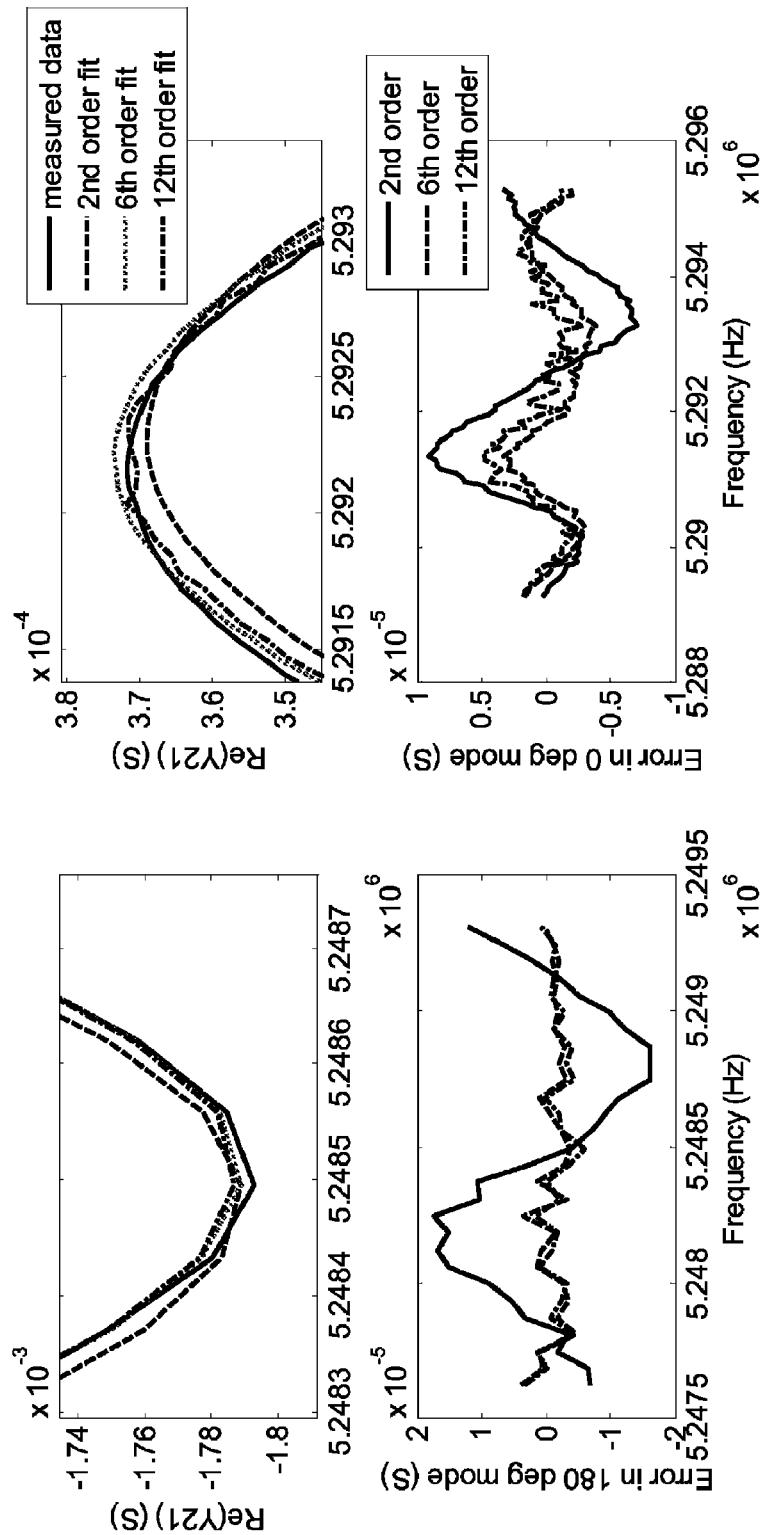
FIG. 15 illustrates the superior results of an inverse-polynomial deconvolution of peaks when the polynomial order is increased from quadratic to $6^{th}$ order and $12^{th}$ order.

FIG. 15 compares inverse-polynomial deconvolution of a two-mode MMQSHR using parabolic, $6^{th}$ order, and $12^{th}$ order polynomials. The data measured for water in a 5 mm cell is shown along with the results of the two-mode, inverse-polynomial fits (top) for the 180° (left) and 0° (right) modes. The residual error (lower) is also shown. For water, which represents an extreme case in the magnitude of the reflected signals, there is some residual error; however over most fluids the $6^{th}$ order polynomial provides an adequate fit. In the previous method, the simpler fit is employed and the error is analyzed to obtain the remaining values. Polynomials offer ease of fitting but do not provide physical insight into the fluid properties, nor are they the best basis functions. In contrast, the analytical model of the equivalent circuit is tedious to curve fit but provides a better correlation to physical properties. The exact choice of basis functions is a matter of technical choice and is not deemed limiting to the invention.

In one variant of this method, inverse-polynomial fits are then used directly to compute the various parameters. In at least one embodiment, the inverse of the real part of the analytical function for the admittance of a single resonant branch is expanded as a Taylor series about the resonant frequency. The analytical expressions for the polynomial coefficients are solved for the desired parameters and the numerical values of the curve fit are employed to compute the associated properties. Combinations of the two approaches may be employed wherein basis functions better suited than inverse parabolic are employed to decompose the transfer function and the basis functions are taken along with the error function to determine the input impedance of a series transmission line and the R-L-C values of the series ideal resonance.

The examples above employed a moderately short fluid path of 5 mm, selected due to constraints of conductivity and dielectric (CD) measurement structures presently in use. The approach of FIG. 9 allows a compact and optimized CD measurement structure with dimensions independent of a larger reflector spacing defining the overall fluid resonance. In at least one embodiment the intentional reflectors are grounded and form a shield around the CD cell. In at least one such environment the inner electrode is perforated and the outer electrode is solid. In one preferred embodiment the sensor is a single sided sensor mounted with flip chip technology to a ceramic carrier and the ceramic carrier also supports the inner and outer CD electrodes.

By allowing compressional waves to pass through the CD electrode structure, the perforated electrodes allow the MMQSHR sensor responses to be intentionally reflected at a path length that differs from the optimum cell geometry of the integrated CD electrodes, as seen in FIG. 9.$b$. For example, the measurement of conductivity and dielectric constant requires large overlap area and small separation to maximize the geometrical factor of the electrode pair. In order to suppress a parasitic cell between the electrodes and the inner electrode and to increase the cell constant while allowing inter-electrode gaps that are conducive to fluid flow, the outer electrode and exposed sensor surface are driven in common as illustrated in FIG. 8.$a$. The formation of a sandwich cell driving the sensor surface and the outer electrode while enclosing the inner electrode minimizes leakage effects and noise. The optimization of the cell constant requires spacings on the order of 0.5-2.0 mm. Significantly smaller spacings risk clogging and significantly larger spacings have low cell constants and high parasitic effects. With 2 mm spacings and 1 mm thick metal, a possible value of 5 mm is seen for the distance to the upper (outer) electrode.

On the other hand, the compressional resonance of a fluid with compressional phase velocity, V, and a reflective opposing surface at a distance, H, has a separation, $\Delta\omega=\pi V/H$, between frequencies of constructive interference with the crystal's shear wave resonance. The number of cycles of inference between the crystal and fluid resonances is $N=\delta\omega/\Delta\omega=\omega_o H/\pi V Q$, where $\omega_o$ is the crystal resonant frequency, Q is the quality factor of the resonance, and the resonance bandwidth, $\delta\omega=Q/\omega_o$. For a 5.25 MHz sensor with a Q of 1000 in water, a height of 5 mm, and a fluid velocity of 1.9 mm/µs, there exists only 0.028 periods or 10 degrees of phase shift of the fluid compressional resonance over the resonator band. Contrasted with the 90° shift of the MMQSHR over this band, there exists an 80° phase differential between the compressional fluid resonance and the crystal shear resonance over the crystal resonance bandwidth. For a perfluoro polyether with a velocity of 0.35 mm/µs the phase shift across a resonance having Q=1000 is 0.164 periods or 60 degrees, resulting in a differential of only 30°. For a mineral oil, in which the resonator Q is reduced to less than 100, there could exist approximately 0.28 periods or 100 degrees of phase shift, resulting in a net differential of −10°. At these spacings, velocities and Q factors, the impedance associated with resonant compressional waves cannot be considered constant over the resonator bandwidth. These phase differentials all result in measurable deviation from the basis function deconvolution into ideal RLC resonances and are all of sufficiently low phase deviation that there will not be periodic ripple in the passband of the resonance. The latter point is important to the use of inverse-polynomial methods and the condition of less than two periods of ripple across the passband is deemed "slow ripple" in this invention. As seen in FIG. 15 there are between 1 and 1.5 periods of ripple in water at 5 mm. Measurements of perfluoro-polyether and mineral oil confirm similar results.

Figure 16:
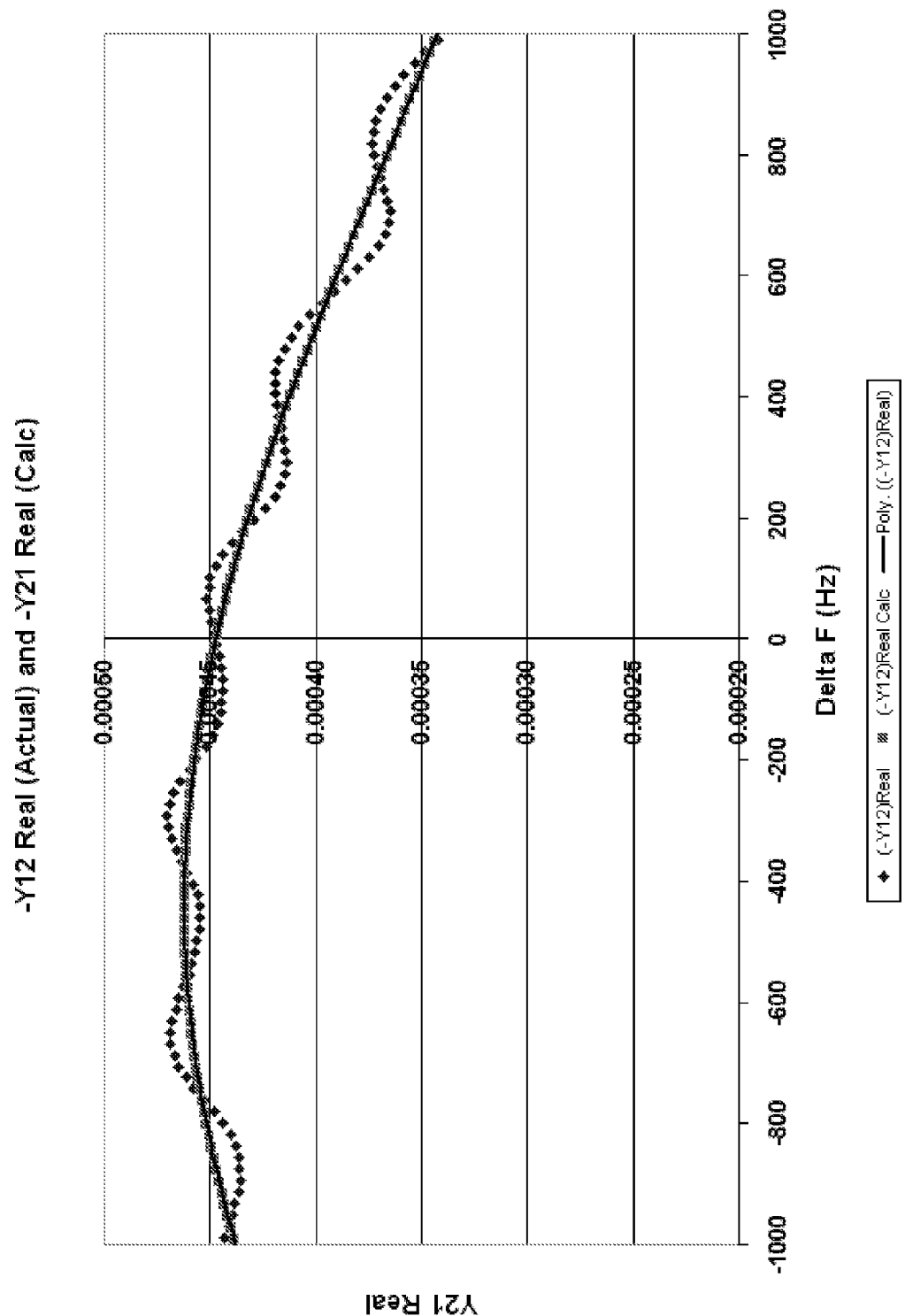
FIG. 16 illustrates the ripple in the measured data of an MMQSHR's transfer conductance due to compressional waveguiding effects.

In very rare cases, data is obtained having a much faster ripple. Measured data with a path length on the order of 5 mm to a fluid-air boundary and a Q of just under 1000 for a water-loaded LGS MMQSHR operating at 5.25 MHz show a 4 KHz bandwidth at half-maximum conductance and a ripple period of 414 Hz, as seen in FIG. 16. From this, it is concluded that there must exist mutual interference between the shear wave resonance and a wave which travelled at least 400 bounces between the piezoelectric and the opposing air-fluid interface. Experimentally it is found that this waveguide mode only exists when the opposing surface is air. The reflection coefficient from a liquid to air is almost perfectly −1; whereas the reflection coefficient between a liquid and steel is only 0.8 to 0.9. The wave would effectively decay by −20 dB within about 20 bounces and by −40 dB in the observed case of 400 bounces.

As such, the existence of fast ripple relative to the bandwidth of the resonator having a relatively short fluid path length is a strong indicator of a liquid-air boundary and may be employed to detect a low fluid level or an air bubble. FIG. 16 also shows the inverse-parabolic basis function curve fit employed to provide the equivalent circuit.

The phase interference factor arises because the MMQSHR transfers energy from an input to an output transducer of the AWD. The acoustic path through the crystal has a phase shift and delay that are determined by the Q of the resonator. The acoustic transmission path through the fluid comprises a waveguide mode trapped between the face of the crystal the opposing fluid boundary that slowly propagates from an input electrode's peak region of shear to compressional mode conversion to the output transducer's peak region of shear to compressional mode conversion. This slow group velocity waveguide mode adds to and subtracts from the resonance transfer function, causing interference and a fast ripple.

In any case, the fast ripple in a short liquid cell is highly sensitive to many factors and is not well suited to instrumentation. This would not be the case of a long fluid cell with a small number of transits, and such a system is contemplated herein. While methods are offered to employ the ripple, it is typically more beneficial to filter it. One such method analyzes the transfer function of the circuit model in FIG. 13 by fitting the overall response to the three subsystems per acoustic mode.

The method involves fitting a measurement to these three subsystems in each resonant circuit path as a function of frequency. In at least one embodiment, the fast ripple terms associated with the waveguide mode are extracted and employed to detect anomalous operation and are then discarded. The remaining solution consists of the traditional RLC branch and the series transmission line input impedance, as discussed above. The slow ripple terms associated with the series transmission line resonance may be employed to detect reflections or to extract information on the velocity, V, propagation loss, α, and acoustic impedance, $Z_o$, of the fluid. Since the velocity is sqrt(κ/ρ) and the fluid compressional impedance is $\theta_m$ sqrt(κρ), the ratio of impedance to velocity yields an estimate of the density and the product obtains the elastic constant of the fluid, provided the impedance ratio, $\theta_m$, of each mode is known. Either of the methods discussed above for treating the primary resonance of the fluid may be employed after filtering.

Figure 17:
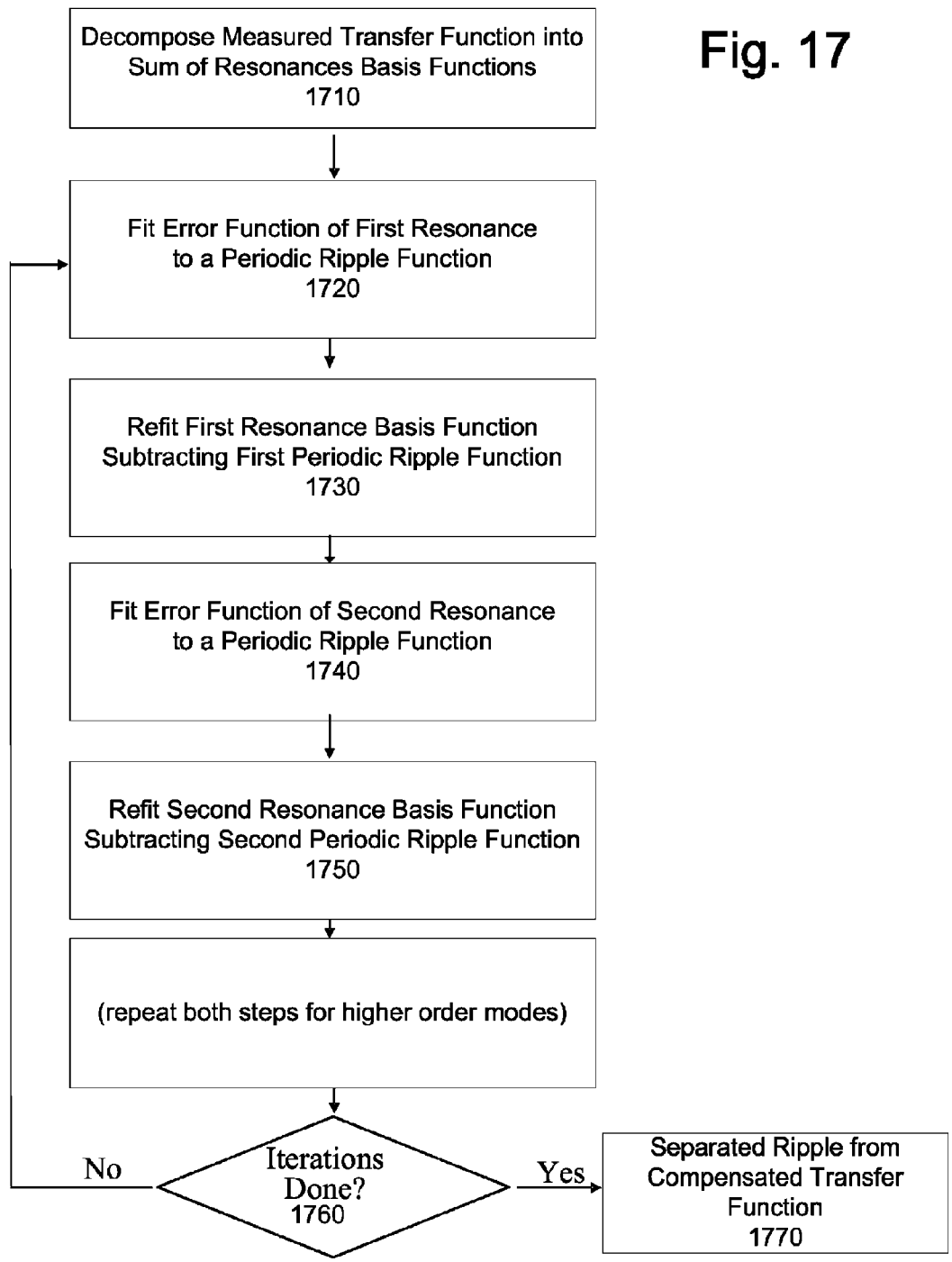
FIG. 17 is a flow chart of the method used to fit the measured data into separate resonant mode basis functions and periodic ripple functions.

The flow chart of this iterative process is shown in FIG. 17. First, the measured transfer function is decomposed into basis functions describing the ideal resonances 1710. Second, the error function about the first resonance is obtained and modeled as an oscillatory ripple function 1720 corresponding to parallel path transmission through a shunt transmission line 1306. Third, the measured transfer function is refit to the basis function of the first resonance after subtracting the ripple 1730. Fourth, error function about the second resonance is obtained and modeled as an oscillatory ripple function 1740 corresponding to parallel path transmission through a shunt transmission line 1305. Fifth, the measured transfer function is refit to the basis function of the first resonance after subtracting the ripple 1750. The process is optionally repeated for third and higher order modes if present. The residual error is evaluated 1760 and iterations repeat 1720-1760 until the error is minimized and the iterations are done. At this point 1770, there exist a series of ripple functions describing the shunt transmission line-induced fast ripple and a compensated, ripple-corrected transfer function describing the series combination of a series R-L-C resonance and a series transmission line stub associated with the primary signal path of each resonant mode. The corrected transfer function is decomposed into basis functions of reach mode resonance and a residual error function, in addition to the periodic ripple functions of each mode.

Using these transmission line parameters corrects the original measurement against the perturbations caused by the ripple. The information describing the ripple can be discarded when the IFFT of the ripple occurs at a time sufficiently greater than 2H/0.350 µs where H is the distance from the crystal to the opposing surface in mm and 0.35 mm/µs is the slowest compressional wave velocity expected for the liquids of interest. In one method, the basis functions are directly employed, with or without the error function, to determine the equivalence circuit parameters.

In another method, described in detail below, the initial correction above is employed in order to eliminate the periodic ripple, followed by a more accurate decomposition into basis functions of sufficient complexity to capture the compressional reflection effects. These second basis functions are then directly employed in calculating the fluid properties.

There exists a method of instrumentation in which the base resonances of the various modes of the MMQSHR and the error functions of each mode are fit to the model of FIG. 13. The pass band ripple described above is assumed to be insignificant, or to already have been filtered and/or compensated from the data by iterative fitting. In one such embodiment, the transfer conductance of the resonance is approximated as before using suitable basis functions for each mode's series R-L-C resonance and the result is subtracted from or divided into the measured data, leaving error terms. The residual error functions are fit to the series stub transmission line impedances. The periodicity and/or curvature of the transfer function terms describing the series transmission line impedance are employed to estimate a time constant of the line, and, coupled with knowledge of the fluid chamber dimensions, offers additional information on physical properties of the intervening fluid, namely the sound velocity. An iterative process is then employed where the estimates of the circuit parameters of the other modes, along with the calculated transmission line parameters, are subtracted from the ripple-corrected measured data and the circuit parameters of the remaining mode re-evaluated is fit to the residual error function.

Figure 18:
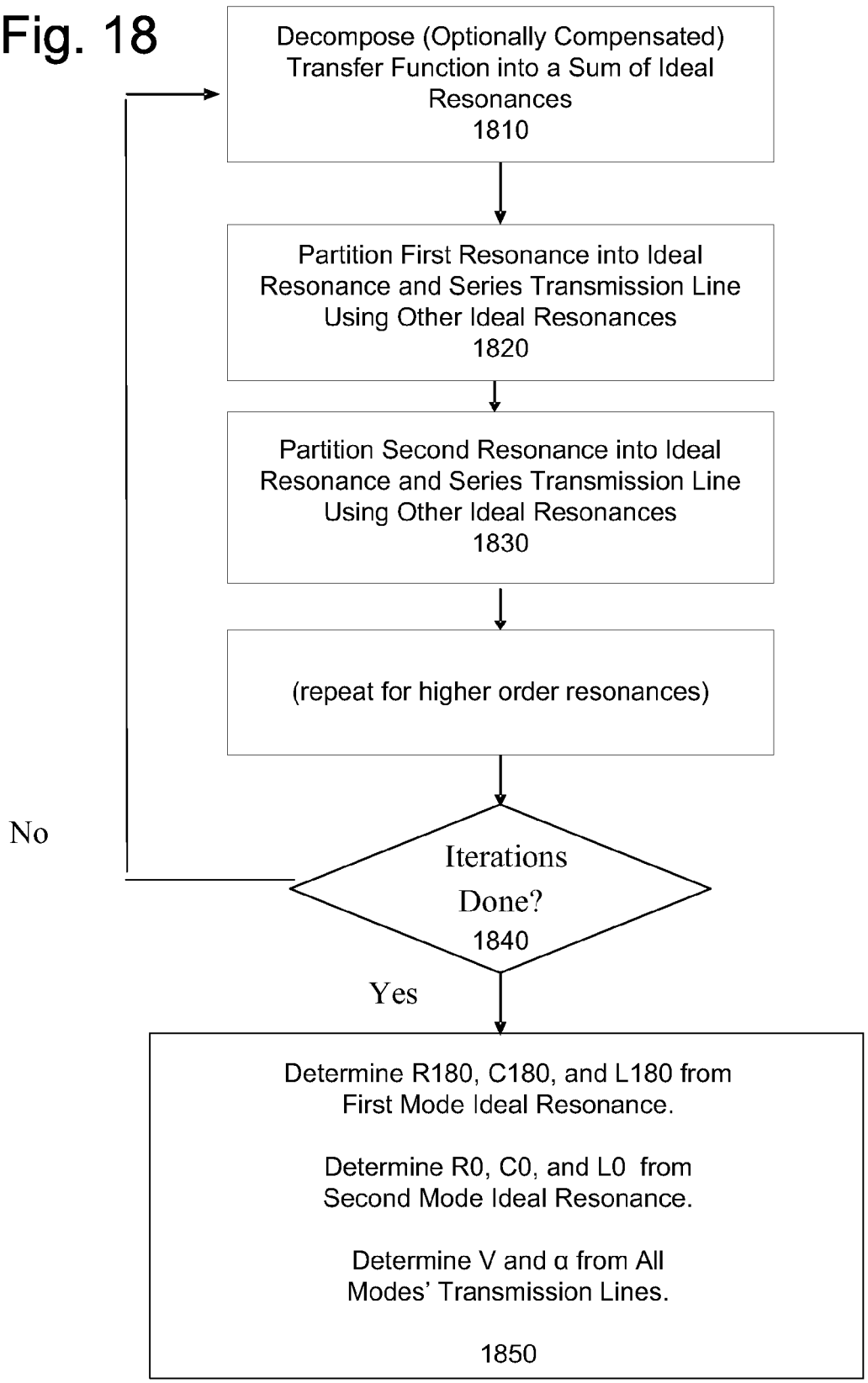
FIG. 18 is a flow chart of the method used to fit the measured data to a sum of resonant mode basis functions and series transmission line properties of the compressional modes in fluid.

FIG. 18 provides a flow chart of an alternate process. The parameters of the shunt transmission lines 1205, 1206 may be ignored as being either insignificant or being already filtered and the data to be fit is the measured transfer function corrected for these ripple terms. First, the basis functions are estimated 1810 from the intervals of the transfer function corresponding to frequency ranges about the resonant frequencies of the at least two modes ignoring transmission line effects on the first iteration. Second, the basis function of the first mode resonance is partitioned into terms associated with the first ideal R-L-C resonance and a first series transmission line 1820. Third, basis function of the second mode resonance is partitioned into terms associated with the second ideal R-L-C resonance and a second series transmission line 1830. Additional modes are optionally partitioned. Iterations 1840 of this successive approximation are taken repeating 1810 through 1830 until the remaining error is minimized 1850. The result is a pair of aggregate basis functions partitioned into basis functions describing the R-L-C resonances and functions describing the series transmission line impedances, themselves. The basis functions are corrected for the distortions of the transmission line stubs, providing compensation for all effects of the reflection. The method may optionally decompose the higher order basis functions to completion, repeating only step 1810 and then partitioning the basis functions into an ideal resonance and series transmission line stub 1820 and 1830 after convergence.

The original parameters, now compensated for the compressional wave reflections, may be employed as proposed in the '868 and '869 applications. Alternately, the full set of fit parameters may be employed in an expansion of the prior art using additional parameters, as detailed below.

FIG. 19 illustrates a preferred method of determining fluid properties from equivalent circuit parameters according to the present invention. The unloaded state measurements proceed as before since the unloaded state is independent of any compressional or viscoelastic effects. Step 1950 provides the fluid to be measured and step 1955 repeats steps 610-630 for the loaded state, except that step 630 employs the addition process of either FIG. 17 or FIG. 18 or a combination thereof instead of the simpler circuit parameter fit of the '869 Application. Steps 1960, 1965, and 1967 create the input parameters. Loss input parameters are defined in detail in the '869 Application and comprise at least the product of motional resistance and motional capacitance. Frequency input parameters are also well defined in the '869 application and comprise at least the product of motional inductance and motional capacitance, which is seen to result in inverse frequency behavior. The new capacitance parameter was identified in the discussions of FIGS. 11.*a* and 11.*b* and is the differential capacitance between the two modes. The velocity parameter is obtained from transmission line terms of FIG. 18, extracted either from the error function as seen in FIG. 14 or from the partitioning a higher-order basis function 1968. The six input parameters are fed to a computing function 1970 and are employed to determine output parameters. Taking the square of the sound velocity as the ratio of elasticity to density, it now becomes possible to separate density from the other measurands, 1975-1995.

Obtaining the fluid compressional velocity expands the system of equations to three with three unknowns and three observables.

$$V_F = \mathrm{sqrt}(\kappa_F/\rho_F)$$

$$Z_C = \mathrm{sqrt}(\kappa_F * \rho_F)$$

$$AV = \mathrm{sqrt}(\rho_F \eta_F)$$

EMBODIMENTS

Embodiments demonstrate the integration of conductivity and dielectric electrodes into a viscometer using thickness shear mode coupled resonators. The approaches are generally applicable to any TSM resonator sensor including single pole resonators, multimode resonators, and the like with either thickness field or lateral field excitation. The approach is applicable to linearly polarized resonators as well as planar torsional sensors and the like, as in J. Andle, R. Haskell, M. Chap, and D. Stevens, "Improved Substrate Selection for Lateral Field TSM Sensors", 2009 IEEE UFFC (unpublished). The well known issues of compressional mode generation are mitigated, and even used to advantage.

It would be further desired to know the compressional elastic modulus in order to better know density and better correct for errors due to compressional wave radiation. In hydraulic systems, compressibility is of direct interest. Martin, S. J. Martin, G. C. Frye, R. W. Cernosek and S. D. Senturia, "Microtextured Resonators for Measuring Liquid Properties," Tech. Digest, Solid-State Sensor and Actuator Workshop, (1994), proposed a method of uniquely measuring density using textured surfaces on one resonator and smooth surfaces on another resonator. Andle, J. Andle, U.S. Pat. No. 7,552,619 B2, "Measurement of Density and Viscoelasticity with a Single Acoustic Wave Sensor", (2005), demonstrated a method using a single, textured, coupled resonator. By texturing the surface of the sensor and employing the zero-crossing frequency between modes 00 and 10 to monitor density, it is possible to use this density data and equation (1) to obtain viscosity, density and compressional modulus, allowing a multi-measurand acoustic wave element with three parameters. In this case, it is desirable to suppress the reflected wave or it could be employed to obtain redundant data for error reduction.

Additionally, this CD ring electrode arrangement can be utilized for any single-mode, single-port TSM resonator or MMQSHR comprising a piezoelectric crystal supporting such modes (LGS, QTZ, etc.) that has sufficient transmitted compressional waves to meet a requirement where a subset of the three electrical parameters ($\Delta R_M$, $\Delta C_M$ and $\Delta L_M$) of at least an $M^{th}$ resonant mode can be utilized to correlate to density/viscosity/elasticity dependent fluid parameters.

U.S. application Ser. No. 12/780,869, entitled "Improved Measurement of Fluid Parameters" discloses a nonlinear combination of these parameters into a "loss parameter", $\omega_{M,air}(R_M C_M - R_{M,air} C_{M,air})$, and a "frequency parameter", $\omega^2_{M,air}(L_M C_M - L_{M,air} C_{M,air}) = (\omega^2_{M,air}/\omega^2_M - 1)$. The motional capacitance is minimally altered in the model and the small changes are systematic in relations to the loss and frequency parameters. While it is best practiced with a coupled resonator such as the MMQSHR, it is also possible to employ these methods with single pole, single port resonators.

Furthermore, this CD ring electrode arrangement can be utilized for any single-port TSM resonator or MMQSHR (LGS, QTZ, etc.) that meets any requirement where a multiple of electrical parameters ($R_M$, $\Delta F$ and L1, etc.) can be utilized to correlate to density/viscosity/elasticity dependent fluid parameters.

Therefore, in one group of embodiments, the opposing surface may be made antireflective, minimizing the magnitude of the ripple and employing installation constraints to render the operationally antireflective perforated electrodes effective in the application. Alternately, the opposing surface may be made optimally reflective and suitably spaced, independent of the optimization of the CD electrode spacings, to provide a sufficient magnitude and periodicity of the constructive and destructive interference with the sensor electrical response.

In another aspect of the invention, reflected signals—intentional or incidental—will have a sufficiently rapid phase shift relative to the main resonance over frequency that the phase mismatch will introduce a periodic distortion to the sensor's transfer function. Whether the electrodes are solid or of parallel ring style, it is desirable to compensate the distortions associated with the reflected signals. In at least one embodiment, the CD electrodes are of parallel ring configuration with a third guard electrode enclosing the measurement cell and providing electrical shielding. It may be undesirable to perforate the shield electrode or otherwise impractical to render it antireflective. In another embodiment the sensor suite may be threaded into an engine block having a potentially reflective surface proximate the aperture of the CD parallel ring electrodes. In either case reflections may be inevitable, and a method of compensating the distortions may be desirable.

Ripple occurs because the measurement is taken at a frequency synchronous with the phase of the transmitted signal via the shear wave resonance whereas the reflected compressional modes return at a phase determined by the highly temperature-dependent sound velocity of the fluid. Over temperature, there is a varying phase difference between the two signals and a pattern of constructive and destructive interference results.

Embodiments provide solutions to integrating viscosity measurement into a multi-measurand sensor that includes a proximate, substantially-parallel, acoustically-reflective surface, such as an electrode or array of electrodes for conductivity and dielectric (CD) measurement cell, without compromise due to compressional wave effects. Additionally, in some embodiments the effects are not only mitigated, but the residual effects are employed to enable additional measurands.

In another embodiment, additional circuit elements are added to the equivalent circuit model of the MMQSHR to account for the ripple. Fitting the more complete model compensates the original model parameters against the ripple introduced by the reflections. In a most preferred embodiment, the additional model parameters are employed to obtain additional physical properties.

This CD parallel ring electrode arrangement can be utilized for any resonator to reduce reflected compressional waves. The most preferred embodiment employs a multi-mode quasi-shear resonator (MMQSR), as described in U.S. application Ser. No. 12/036,125, with multiple modes that produce a multiplicity of electrical output responses that can be correlated to density/viscosity/elasticity dependent fluid parameters. In the most preferred embodiment, the MMQSR is a two-port, multi-pole resonator.

It may also be desirable, instead, to employ the reflected signal as a compressional wave probe of the fluid properties. In particular, U.S. application Ser. No. 12/036,125 and Ser. No. 12/540,339 detail an approach to measure ($\rho\eta$) and ($\rho C_F$) but must assume knowledge of one variable in order to quantify the other two. In the present invention, a third measurand is offered that obtains ($C_F/\rho$), allowing complete knowledge of all three physical properties. The frequency periodicity of the ripple introduced into the resonator's transfer function is inversely related to the length of the propagation path in the fluid. Low loss fluids resulting in high Q resonances require long fluid cells whereas high viscosity fluids having broad resonances can tolerate, and even require, short propagation paths in the fluid.

In one embodiment, the CD electrodes are both solid and the compressional wave is immediately reflected back to the surface. In another embodiment, one or more parallel plates are perforated to allow a longer fluid propagation path.

Other embodiments provide a multi-measurand sensor system comprising a thickness shear mode (TSM) resonator sensor; at least one proximate, effectively parallel, acoustically reflective surface; a fluid in region the at least one surface; and wherein at least one electrode reflects acoustic waves, the system providing for compressional wave effects whereby multiple measurements are not compromised due to compressional wave effects.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A method for simultaneous determination of physical properties of a fluid utilizing an acoustic wave device (AWD) sensor having at least two resonant modes, said modes comprising predominantly horizontally polarized shear waves, comprising the steps of:
    measuring a transfer function of said AWD sensor over a frequency range of interest about at least two resonant frequencies corresponding to said at least two resonant modes;
    decomposing said measured transfer function into basis functions, each of said basis functions being descriptive of a specific resonance of said AWD sensor; and
    deriving said physical properties of said fluid from coefficients of said basis functions describing said measured transfer function of said AWD sensor,
    wherein at least one of said basis functions is further descriptive of finite-geometry fluid resonance, and
    wherein said at least one of said basis functions incorporates a frequency dependence of said measured transfer function deviating from a lumped element equivalent circuit.

2. The method of claim 1 comprising:
    decomposing said measured transfer function into basis functions describing ideal resonances in absence of reflections;
    obtaining error function about a first resonance, being a deviation between measured data and sum of said basis functions, then modeling said error function as a first oscillatory function;
    refitting said measured transfer function to a first basis function of a first resonance after subtracting said first oscillatory function from measured data;
    obtaining error functions about additional resonances, being differences between said measured data and said sum of said basis functions, then modeling said error functions as additional oscillatory functions;
    refitting said measured transfer function to additional basis functions of said additional resonances after subtracting said additional oscillatory functions from said measured data in each frequency interval about said additional resonances;
    evaluating residual error;
    repeating said steps of obtaining an error function about a first resonance, refitting error-compensated first resonance to a basis function, obtaining an error function about each of additional resonances, again refitting each of said error-compensated additional resonances to additional basis functions, and evaluating until said error is minimized; and
    obtaining basis functions descriptive of each selected resonant mode of said transfer function compensated for errors from reflections.

3. The method of claim 1, comprising:
    expressing at least one of said basis functions as sum of a series resonance basis function and a transmission line basis function,
    estimating basis functions from intervals of a transfer function corresponding to frequency ranges about resonant frequencies of said at least two modes, ignoring transmission line effects on first iteration;
    partitioning basis function of first mode resonance into terms associated with a first ideal R-L-C resonance and a first series transmission line;
    partitioning basis function of additional mode resonances into terms associated with additional ideal R-L-C resonances and additional series transmission lines;
    repeating said steps of estimating, partitioning said basis function of said first mode resonance, and partitioning said basis function of said additional mode resonances until remaining error is minimized; and
    determining parameters from ideal resonances of said at least two modes, and from transmission line of at least one mode, said parameters reflective of said physical properties of said fluid.

4. The method of claim 2 comprising:
    determining compressional wave velocity of said fluid from periodicity of said oscillatory functions knowing separation distance (H).

5. The method of claim 2 comprising:
    ignoring said oscillatory functions and,
    employing coefficients of said basis functions to obtain input parameters to a computing function, outputs of which are representative of said physical properties of said fluid, wherein said input parameters are compensated for distortions of ripple.

6. The method of claim 5, further wherein said basis functions employed are sufficiently accurate to incorporate influence of fluid resonances, further comprising:
    decomposing a compensated transfer function comprising a sum of said basis functions into a sum of new basis functions, each of said new basis functions being descriptive of a specific resonance of said AWD;
    deriving said physical properties of said fluid from coefficients of said new basis functions of said AWD sensor;
    wherein at least one new basis function is further descriptive of said finite-geometry fluid resonance;
    wherein said at least one basis function incorporates a frequency dependence of said transfer function deviating from said lumped element equivalent circuit; further comprising:
    expressing at least one of said new basis functions as sum of a series resonance basis function and a transmission line basis function;
    estimating said new basis functions from the intervals of the said compensated transfer function corresponding to frequency ranges about resonant frequencies of SAID at least two modes, ignoring transmission line effects on first iteration;
    partitioning said new basis function of said first mode resonance into terms associated with a first ideal R-L-C resonance and a first series transmission line;
    partitioning said new basis function of said additional mode resonances into terms associated with additional ideal R-L-C resonances and additional series transmission lines;
    repeating said steps of estimating, partitioning said basis function of said first mode resonance, and partitioning SAID basis function of SAID additional mode resonances until remaining error is minimized; and
    determining parameters from ideal resonances of said at least two modes, and from transmission line of at least one mode, said parameters reflective of said fluid properties.

7. The method of claim 3, further comprising:
decomposing said transfer function into families of at least one basis function, each of said families being descriptive of a specific resonance of said AWD, and each said transfer function within said family being descriptive of a fluid-device interaction for said resonance.

8. The method of claim 3, wherein different basis functions are employed on at least two successive iterations, producing a final decomposition.

9. The method of claim 6, wherein different new basis functions are employed on at least two successive iterations, producing a final decomposition.

10. The method of claim 1, wherein employing said coefficients of said basis functions to obtain input parameters to a computing function, outputs of which are representative of said physical properties of said fluid, comprises:
wherein at least two of said input parameters are loss parameters,
wherein at least two of said input parameters are frequency parameters,
wherein at least one of said input parameters is a function of motional capacitance of a first resonance, said function being linearly independent of other input parameters, and
wherein at least one of said input parameters is a function of motional capacitance of a second resonance, said function being linearly independent of said other input parameters.

11. An acoustic wave device (AWD) sensor for simultaneous determination of fluid properties, said device comprising:
at least one solid structure opposite a surface of said AWD, defining finite extents of a fluid to be measured, said structure being anti-reflective to compressional waves propagating away from said surface of said AWD, preventing reflection of compressional waves that would interact with said AWD, thereby altering response of said AWD,
and allowing dual mode viscosity sensor responses to be utilized for measurement of said fluid properties and correlation.

12. The device of claim 11, wherein said AWD is loaded with fluid on both surfaces and said at least one solid structure comprises solid structures opposite both surfaces of said AWD.

13. The device of claim 11, wherein said solid structure opposite a surface of said AWD comprises apertures allowing compressional waves to propagate away from said surface of said AWD unimpeded, preventing reflection of compressional waves that would interact with said AWD, thereby altering response of said AWD;
said apertures allowing compressional waves to pass through said solid structure and being effectively anti-reflective, and allowing dual mode viscosity sensor responses to be utilized for measurement of said fluid properties and correlation.

14. The device of claim 11, wherein said solid structure opposite a surface of said AWD comprising textures, said textures randomly reflecting said compressional waves, preventing coherent reflection of said compressional waves that would interact with said AWD, thereby altering response of said AWD;
said textures being effectively anti-reflective, and allowing dual mode viscosity sensor responses to be utilized for measurement of said fluid properties and correlation.

15. The device of claim 11, comprising an antireflective layer disposed upon said solid surface.

16. The device of claim 11, wherein said solid structure comprises at least one electrode of an integrated subsystem for measuring fluid electrical properties.

17. The device of claim 15, wherein said antireflective layer on said solid surface comprises one electrode of an integrated subsystem for measuring fluid electrical properties.

18. The device of claim 11, comprising antireflective supports.

19. The device of claim 11, wherein said measurement of fluid properties comprises at least one of fluid density, fluid viscosity, fluid relaxation time, fluid sound velocity, fluid acoustic attenuation, and fluid elasticity.

20. A multi-measurand fluid sensor system comprising:
a multi-mode, quasi-shear-horizontal resonator (MM-QSHR) AWD sensor;
at least one proximate, effectively parallel, acoustically reflective surface;
a fluid in a region between a surface of said sensor and said at least one surface; and
wherein said at least one acoustically reflective surface reflects acoustic waves, said system providing for compressional wave resonances between said AWD and said acoustically reflective surface, said compressional fluid resonances coupled to said sensor quasi-shear-horizontal resonances,
said compressional fluid resonances altering nominal transfer function of said sensor, said alterations being independently reflective of density of said fluid and compressional elastic modulus of said fluid.

21. The sensor system of claim 20, wherein a surface of said resonator is contoured, being functionally parallel to an acoustically reflective surface.

22. The sensor system of claim 20 wherein said at least one acoustically reflective surface comprises an electrode of a measurement cell for determining electrical properties of said fluid.

23. The sensor system of claim 22 wherein said surface of said sensor comprises an electrode of a measurement cell for determining electrical properties of said fluid.

24. The sensor system of claim 20 wherein at least one perforated solid structure is located between said surface of said AWD and said acoustically reflective surface.

25. The sensor system of claim 24 wherein said at least one perforated solid structure comprise electrodes for a measurement cell for determining electrical properties of said fluid.

26. The sensor system of claim 20 wherein said sensor is located between two mutually reflective surfaces, forming a compressional resonance therebetween.

27. The sensor system of claim 20, comprising separation value (H) selected such that, at a nominal operating temperature and fluid composition, input impedance of resonance of said fluid is purely real.

28. The sensor system of claim 27, wherein said input impedance corresponds to a minimum compressional motional resistance.

29. The sensor system of claim 27, wherein said input impedance corresponds to a maximum compressional motional resistance.

* * * * *